United States Patent
Rearick

(10) Patent No.: US 11,657,893 B2
(45) Date of Patent: *May 23, 2023

(54) MODELS FOR ANALYZING DATA FROM SEQUENCING-BY-SYNTHESIS OPERATIONS

(71) Applicant: LIFE TECHNOLOGIES CORPORATION, Carlsbad, CA (US)

(72) Inventor: Todd Rearick, Cheshire, CT (US)

(73) Assignee: Life Technologies Corporation, Carlsbad, CA (US)

( * ) Notice: Subject to any disclaimer, the term of this patent is extended or adjusted under 35 U.S.C. 154(b) by 377 days.

This patent is subject to a terminal disclaimer.

(21) Appl. No.: 15/929,565

(22) Filed: May 11, 2020

(65) Prior Publication Data
US 2020/0342952 A1    Oct. 29, 2020

Related U.S. Application Data

(60) Continuation of application No. 15/498,591, filed on Apr. 27, 2017, now Pat. No. 10,679,724, which is a
(Continued)

(51) Int. Cl.
*G01N 33/48*     (2006.01)
*G01N 33/50*     (2006.01)
(Continued)

(52) U.S. Cl.
CPC .............. *G16B 5/00* (2019.02); *C12Q 1/6874* (2013.01); *G16B 25/00* (2019.02); *G16B 30/00* (2019.02)

(58) Field of Classification Search
CPC .......... G16B 5/00; G16B 25/00; G16B 30/00; C12Q 1/6874
See application file for complete search history.

(56) References Cited

U.S. PATENT DOCUMENTS

| 4,384,273 A | 5/1983 | Ackland et al. |
| 4,683,195 A | 7/1987 | Mullis et al. |

(Continued)

FOREIGN PATENT DOCUMENTS

| GB | 2461127 A | 12/2009 |
| JP | H04262799 A | 9/1992 |

(Continued)

OTHER PUBLICATIONS

454 Sequencing System Software Manual Version 2.6 Part B : GS Run Processor, GS Reporter, GS Run Browser, GS Support Tool, available at http://genepool.bio.ed.ac.uk/Gene_Pool/454_software/Manuals/454SeqSys_SWManualv2.6 PartB May 2011.pdf (last visited Aug. 31, 2012) (document dated May 2011 ).
(Continued)

*Primary Examiner* — Russell S Negin

(57) ABSTRACT

A method of modeling a background signal when sequencing a polynucleotide strand using sequencing-by-synthesis includes: flowing a series of nucleotide flows onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; receiving output signals from the reactor array; and modeling a background signal for the loaded reaction confinement region using the received output signals and a model adapted to account at least for an exchange of ions between the one or more neighboring reaction confinement regions and a headspace adjacent the loaded reaction confinement region and the one or more neighboring reaction confinement regions.

18 Claims, 15 Drawing Sheets

FIG. 1A

Related U.S. Application Data division of application No. 13/892,116, filed on May 10, 2013, now Pat. No. 9,646,132.

(60) Provisional application No. 61/645,951, filed on May 11, 2012.

(51) Int. Cl.
   *G16B 5/00* (2019.01)
   *C12Q 1/6874* (2018.01)
   *G16B 25/00* (2019.01)
   *G16B 30/00* (2019.01)

(56) References Cited

U.S. PATENT DOCUMENTS

| | | | |
|---|---|---|---|
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,587,128 A | 12/1996 | Wilding et al. | |
| 5,750,341 A | 5/1998 | Macevicz | |
| 5,854,033 A | 12/1998 | Lizardi | |
| 6,033,546 A | 3/2000 | Ramsey | |
| 6,054,034 A | 4/2000 | Soane et al. | |
| 6,174,670 B1 | 1/2001 | Wittwer et al. | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,399,952 B1 | 6/2002 | Maher et al. | |
| 6,404,907 B1 | 6/2002 | Gilchrist et al. | |
| 6,613,525 B2 | 9/2003 | Nelson et al. | |
| 6,780,591 B2 | 8/2004 | Williams et al. | |
| 6,828,100 B1 | 12/2004 | Ronaghi | |
| 6,833,246 B2 | 12/2004 | Balasubramanian | |
| 6,911,327 B2 | 6/2005 | McMillan et al. | |
| 6,960,437 B2 | 11/2005 | Enzelberger et al. | |
| 7,037,687 B2 | 5/2006 | Williams et al. | |
| 7,049,645 B2 | 5/2006 | Sawada et al. | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 9,646,132 B2 * | 5/2017 | Rearick | G16B 30/00 |
| 10,146,906 B2 | 12/2018 | Rearick et al. | |
| 10,679,724 B2 * | 6/2020 | Rearick | C12Q 1/6874 |
| 2003/0219797 A1 | 11/2003 | Zhao et al. | |
| 2003/0232354 A1 | 12/2003 | Yu et al. | |
| 2004/0018506 A1 | 1/2004 | Koehler et al. | |
| 2004/0197793 A1 | 10/2004 | Hassibi et al. | |
| 2004/0197845 A1 | 10/2004 | Hassibi et al. | |
| 2005/0084851 A1 | 4/2005 | Ronaghi et al. | |
| 2006/0040297 A1 | 2/2006 | Leamon et al. | |
| 2006/0147935 A1 | 7/2006 | Linnarsson | |
| 2006/0147983 A1 | 7/2006 | O'Uchi | |
| 2007/0059733 A1 | 3/2007 | Sundararajan et al. | |
| 2007/0059741 A1 | 3/2007 | Kamahori et al. | |
| 2007/0092872 A1 | 4/2007 | Rothberg et al. | |
| 2007/0207471 A1 | 9/2007 | Osaka et al. | |
| 2007/0219367 A1 | 9/2007 | Shchepinov et al. | |
| 2007/0281300 A1 | 12/2007 | Russell et al. | |
| 2008/0166727 A1 | 7/2008 | Esfandyarpour et al. | |
| 2008/0182757 A1 | 7/2008 | Heiner et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2010/0035252 A1 | 2/2010 | Rothberg et al. |
| 2010/0035763 A1 | 2/2010 | Chen et al. |
| 2010/0075327 A1 | 3/2010 | Maxham et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0183320 A1 | 7/2011 | Flusberg et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2013/0060482 A1 | 3/2013 | Sikora et al. |
| 2013/0090860 A1 | 4/2013 | Sikora et al. |
| 2013/0303384 A1 | 11/2013 | Rearick |
| 2017/0293713 A1 | 10/2017 | Rearick |

FOREIGN PATENT DOCUMENTS

| | | |
|---|---|---|
| WO | WO-1999019717 A1 | 4/1999 |
| WO | WO-9957321 A1 | 11/1999 |
| WO | WO-0220837 A2 | 3/2002 |
| WO | WO-2002024322 A2 | 3/2002 |
| WO | WO-03020895 A2 | 3/2003 |
| WO | WO-2004001015 A2 | 12/2003 |
| WO | WO-2005040425 A2 | 5/2005 |
| WO | WO-2007098049 A2 | 8/2007 |
| WO | WO-2008076406 A2 | 6/2008 |
| WO | WO-2008092150 A1 | 7/2008 |
| WO | WO-2008092155 A2 | 7/2008 |
| WO | WO-2009117119 A1 | 9/2009 |
| WO | WO-2009158006 A2 | 12/2009 |
| WO | WO-2010047804 A1 | 4/2010 |
| WO | WO-2010077859 A2 | 7/2010 |
| WO | WO-2010117804 A2 | 10/2010 |
| WO | WO-2010138182 A2 | 12/2010 |
| WO | WO-2011120964 A1 | 10/2011 |
| WO | WO-2011156707 A2 | 12/2011 |

(56) References Cited

FOREIGN PATENT DOCUMENTS

| WO | WO-2012058459 A2 | 5/2012 |
|---|---|---|
| WO | WO-2012092515 A2 | 7/2012 |

OTHER PUBLICATIONS

Ahmadian et al., "Pyrosequencing: History, biochemistry and future," Clinica Chimica Acta, 363:83-94 (2006).

Anderson et al., "A system for multiplexed direct electrical detection of DNA synthesis", Sensors and Actuators B: Chemical, vol. 129, No. 1, Jan. 2008, pp. 79-86.

Balzer et al., "Characteristics of 454 pyrosequencing data-enabling realistic simulation with flowsim," Bioinformatics, 26:i420-i425 (2010).

Barbaro et al., "Fully electronic DNA hybridization detection by a standard CMOS biochip", Sensors and Actuators B: Chemical, vol. 118, 2006, pp. 41-46.

Brockman et al., "Quality scores and SNP detection in sequencing-by-synthesis systems," Genome Research, 18:763-770 (2008).

Chapter 2, "Machine-Learning Foundations: The Probabilistic Framework", In: Baldi, P. and Brunak, S., "Bioinformatics: The Machine Learning Approach, 2"d Edition, The MIT Press, 47-65 (2001).

Eltoukhy, H., et al., "Modeling and Base-Calling for DNA Sequencing-By-Synthesis", 2006 IEEE International Conference on Acoustics, Speech, and Signal Processing, vol. 2, May 2006, II-1032-II-1035.

Finotello et al., "Comparative analysis of algorithms for whole-genome assembly of pyrosequencing data," Briefings in Bioinformatics Advance Access, 1-12 (Oct. 21, 2011 ).

Hammond et al., "Design of a Single-Chip pH Sensor Using a Conventional 0.6-.mu.m CMOS Process", IEEE Sensors Journal, vol. 4, No. 6, 2004, pp. 706-712.

Hammond et al., "Performance and system-on-chip integration of an unmodified CMOS ISFET", Sensors and Actuators B: Chemical, vols. 111-112, Nov. 2005, pp. 254-258.

Heer et al., "Single-chip microelectronic system to interface with living cells," Biosensors and Bioelectronics, 22:2546-2553 (2007).

Hert et al., "Advantages and limitations of next-generation sequencing technologies: a comparison of electrophoresis and non-electrophoresis methods," Electroghoresis, 29(23):4618-26 (2008).

Hizawa et al., "Fabrication of a two-dimensional pH image sensor using a charge transfer technique", Sensors and Actuators B: Chemical, vol. 117, No. 2, Oct. 2006, pp. 509-515.

Hughes, R C. et al., "Chemical Microsensors", Science, vol. 254, Doc rec'd from Christian D'Avignon-Aubut; CDA prepared final SB08, 1991, pp. 74-80.

Huse et al., "Accuracy and quality of massively parallel DNA pyrosequencing," Genome Biology, 8(7):R143.1-R143.9 (2007).

International Search Report and Written Opinion in PCT/US2011/067776, dated Jul. 13, 2012, 11 pages.

Ji et al., "BM-BC: A Bayesian method of base calling for Solexa sequence data," Department of Biostatistics, The University of Texas M. D. Anderson Cancer Center, Houston, Texas, U.S.A. (http://odin.mdacc.tmc.edu/-ylii/BMBC/bmbc-ie2.pdf), 1-27, 2010.

Kao et al., "BayesCall: A model-based base-calling algorithm for high-throughput short-read sequencing," Genome Research, vol. 19, No. 10, Oct. 2009,1884-1895.

Langaee et al., "Genetic variation analyses by Pyrosequencing," Mutation Research, 573: 96-102 (2005).

Leamon et al., "Cramming More Sequencing Reactions onto Microreactor Chips", Chemical Reviews, vol. 107, No. 8, Aug. 2007, pp. 3367-3376.

Ledergerber et al., "Base-calling for next-generation sequencing platforms," Briefings in Bioinformatics Advance Access, 12(5):489-497 (Jan. 18, 2011 ).

Lewis, et al., "Sequence analysis of the cis-regulatory regions of the bithorax complex of *Drosophila*", Proc. Natl. Acad. Sci. USA, vol. 92, Aug. 1995, pp. 8403-8407.

Lysholm et al., "FAAST: Flow-space Assisted Alignment Search Tool," BMC Bioinformatics 2011,12:293 (http://www.biomedcentral.com/1471-2105/12/293), pp. 1-7 (2011).

Margulies et al., "Supplemental Materials, Genome Sequencing in Microfabricated High-Density Picolitre Reactors", Nature, vol. 437, No. 15, 2005, pp. 1-34.

Martinoia et al., "Development of ISFET Array-Based Microsystems for Bioelectrochemical measurements of cell populations", Biosensors & Bioelectronics, vol. 16, Nos. 9-12, Dec. 2001, pp. 1043-1050.

Massingham et al., "All Your Base: a fast and accurate probabilistic approach to base calling," Euroclean Bioinformatics Institute, Wellcome Trust Genome Cam12us, Hinxton, Cambridgeshire, UK (http://www.ebi.ac.uk/goldman-srv/AYB/references/ayb_revised.pdf), Oct. 26, 2011, 1-26.

Metzker, "Emerging technologies in DNA sequencing," Genome Research, 15:1767-1776 (2005).

Mikolajick et al. The pH-sensing properties of tantalum pentoxide films fabricated by metal organic low pressure chemical vapor deposition. Sensors and Actuators B, vol. 44, 1997, pp. 262-267.

Milgrew et al., "A large transistor-based sensor array chip for direct extracellular imaging", Sensors and Actuators B: Chemical, vols. 111-112, Nov. 2005, pp. 347-353.

Milgrew et al., "The Development of Scalable Sensor Arrays Using Standard CMOS Technology", Sensors and Actuators B: Chemical, vol. 103, Nos. 1-2, Sep. 2004, pp. 37-42.

Mir et al., "Integrated electrochemical DNA biosensors for lab-on-a-chip devices," Electrophoresis, 30:3386-3397 (2009).

Pourmand et al., "Direct electrical detection of DNA synthesis", Proceedings of the National Academy of Sciences, vol. 103, No. 17, Apr. 2006, pp. 6466-6470.

Ronaghi et al., "A Sequencing Method Based on Real-Time Pyrophosphate", Science, vol. 281, No. 5375, Jul. 1998, pp. 363-365.

Ronaghi, "Pyrosequencing Sheds Light on DNA Sequencing," Genome Research, 11:3-11 (2001).

Svantesson et al., "A mathematical model of the Pyrosequencing reaction system," Biophysical Chemistry, 100:129-145 (2004).

Trojanowicz, "Recent developments in electrochemical flow detections—a review: part I. Flow analysis and capillary electrophoresis," Anal. Chim. Acta, 653(1 ):36-58 (2009).

Woias, "Modelling the short time response of ISFET sensors", Sensors and Actuators B: Chemical, vol. 24, Nos. 1-3, Mar. 1995, pp. 211-217.

Xu et al., "Integration of electrochemistry in micro-total analysis systems for biochemical assays: recent developments," Talanta, 80(1):8-18 (2009).

Yeow et al., "A very large integrated pH-ISFET sensor array chip compatible with standard CMOS processes", Sensor and Actuators B: Chemical, vol. 44, Nos. 1-3, Oct. 1997, pp. 434-440.

\* cited by examiner

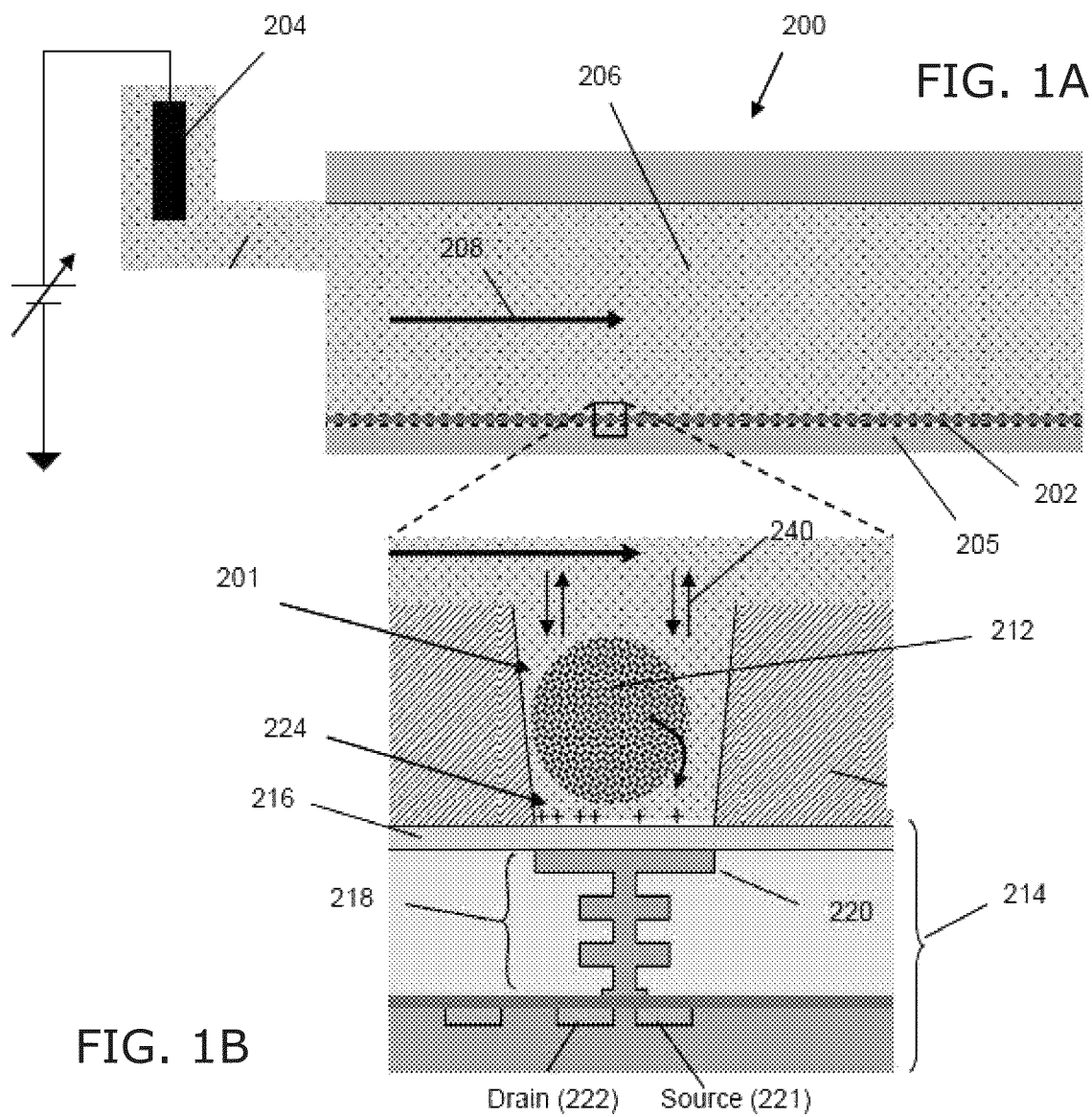

FIG. 2A
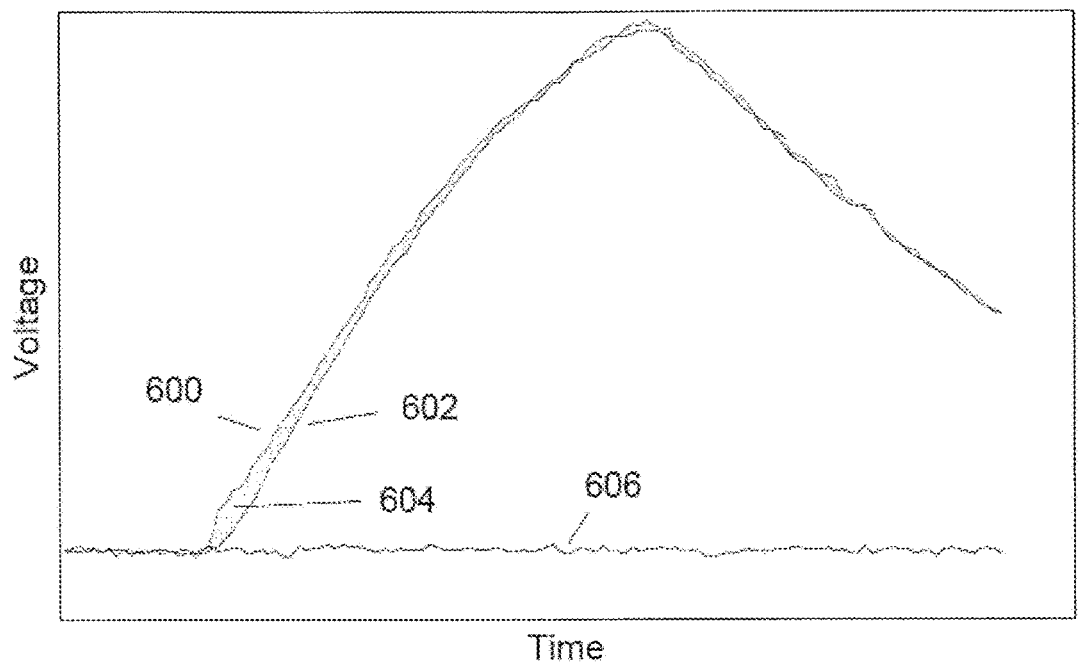
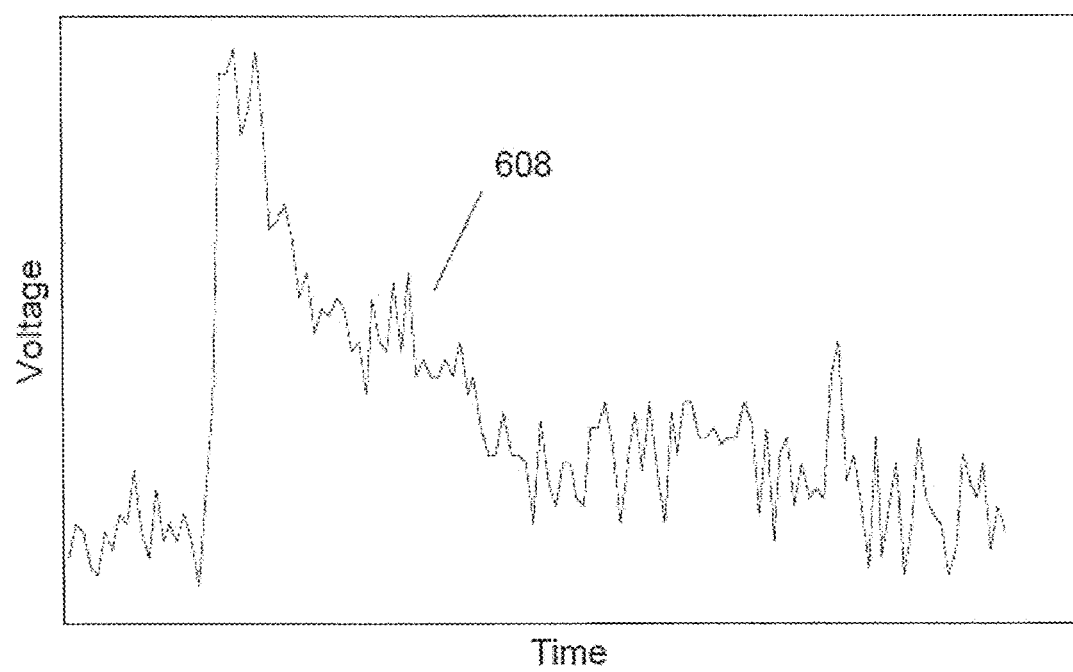
FIG. 2B

FIG. 3
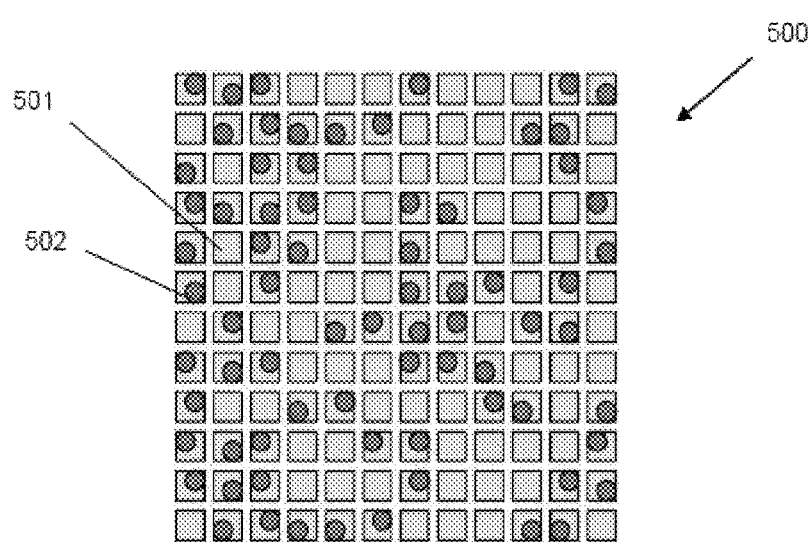
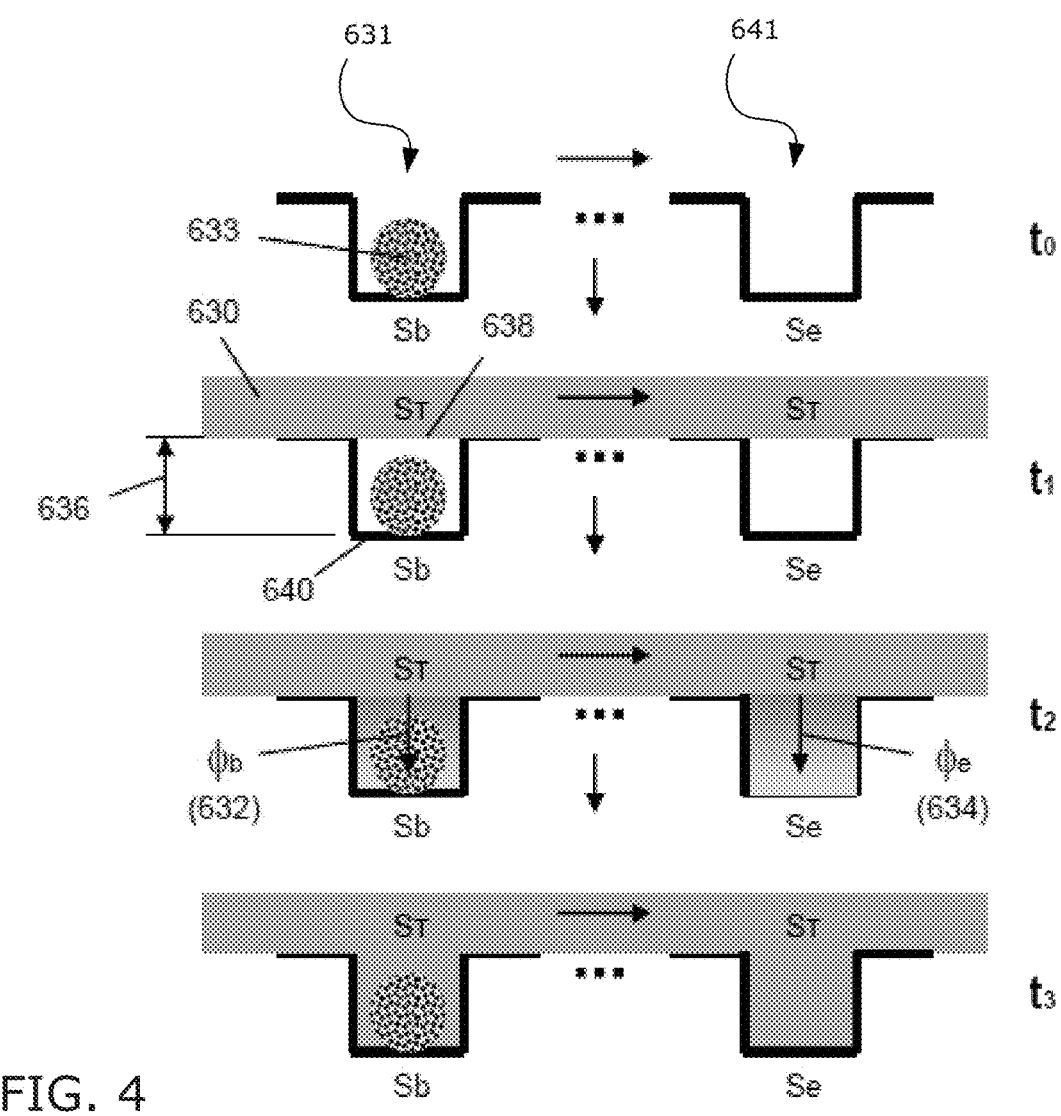
FIG. 4

FIG. 8C
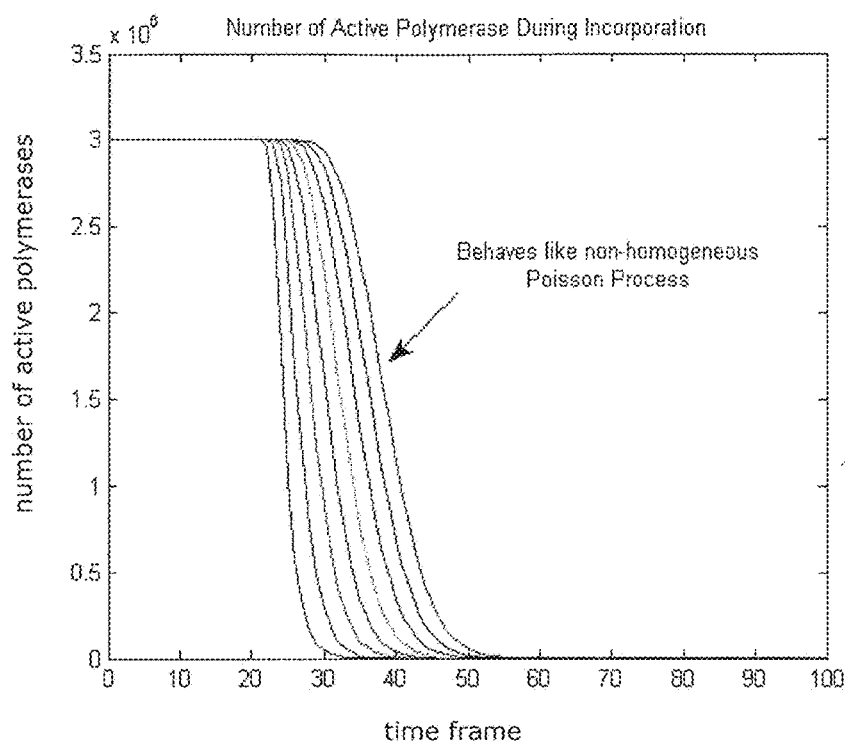
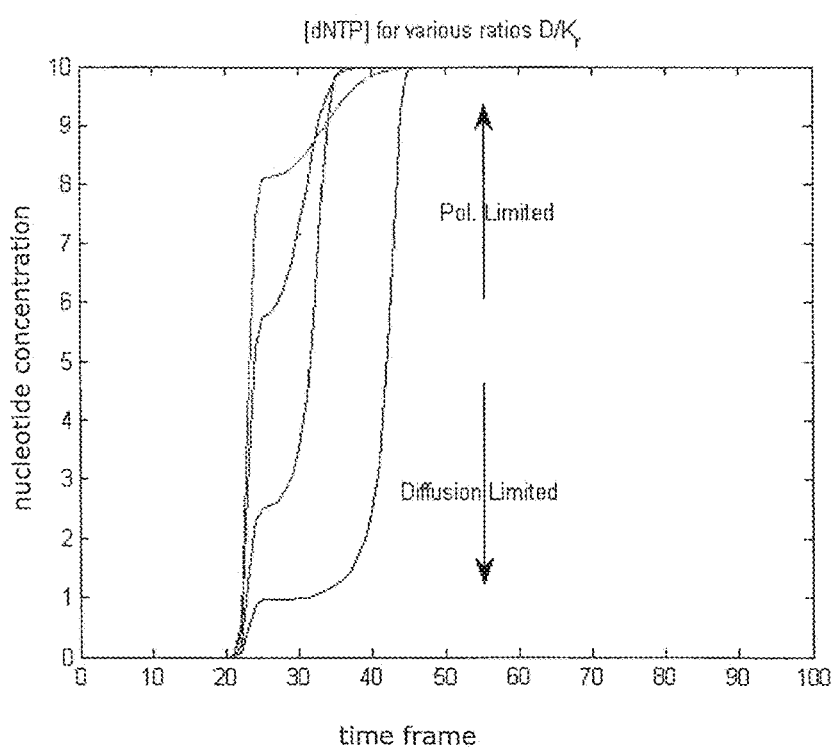
FIG. 8D

MODELS FOR ANALYZING DATA FROM SEQUENCING-BY-SYNTHESIS OPERATIONS

CROSS-REFERENCE TO RELATED APPLICATIONS

This application is a continuation of U.S. patent application Ser. No. 15/498,591 filed Apr. 27, 2017, which is a division of U.S. patent application Ser. No. 13/892,116 filed May 10, 2013, now U.S. Pat. No. 9,646,132, which claims the benefit of U.S. patent application No. 61/645,951 filed May 11, 2012, which disclosures are herein incorporated by reference in their entirety.

TECHNICAL FIELD

The present application generally relates to nucleic acid sequencing, and more particularly, to models for analyzing data from nucleic acid sequencing operations.

BACKGROUND

Sequencing-by-synthesis is among a new generation of high throughput DNA sequencing technologies. Examples of techniques and platforms for sequencing-by-synthesis include the Genome Analyzer/HiSeq/MiSeq platforms (Illumina, Inc.; see e.g., U.S. Pat. Nos. 6,833,246 and 5,750,341); those applying pyrosequencing-based sequencing methods such as that used by Roche/454 Technologies on the GS FLX, GS FLX Titanium, and GS Junior platforms (see e.g., Ronaghi et al., SCIENCE, 281:363 (1998) and Margulies et al., NATURE, 437:376-380 (2005)); and those by Life Technologies Corp./Ion Torrent in the PGM™ system (see e.g., U.S. Patent Application Publication No. 2010/0137143 and No. 2009/0026082, which are both incorporated by reference herein in their entirety). There is a need for improved signal processing techniques to process signal data from sequencing-by-synthesis operations.

BRIEF DESCRIPTION OF THE DRAWINGS

The accompanying drawings illustrate one or more exemplary embodiments of the present invention and serve to explain the principles of various exemplary embodiments. The drawings are exemplary and explanatory only and are not in any way limiting of the present invention.

FIGS. 1A and 1B show an exemplary section of a flow cell and a microwell.

FIG. 2A shows a plot of output signals from different wells on an exemplary sensor array; FIG. 2B shows an example of an incorporation signal.

FIG. 3 shows a random distribution of loaded wells and empty wells on an exemplary reactor array.

FIG. 4 shows two neighboring microwells and the diffusion of hydrogen ions into the microwells.

FIGS. 8A-8D show behavioral characteristics of an incorporation signal model according to an exemplary embodiment.

SUMMARY

Figure 5A:
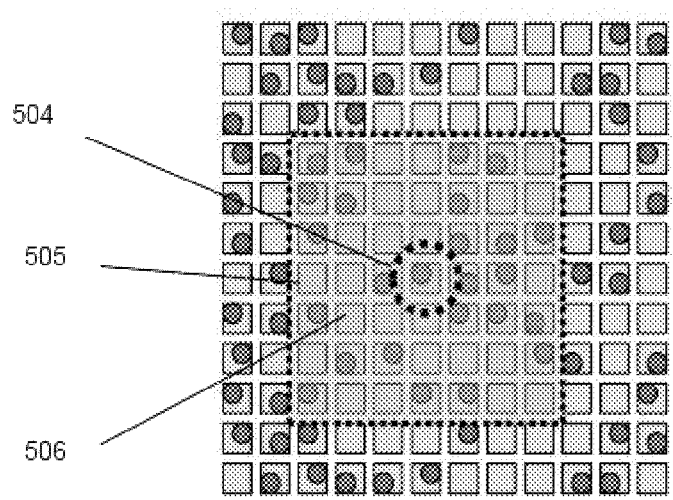
FIGS. 5A and 5B show examples of neighborhood regions on an exemplary reactor array.

According to an exemplary embodiment, there is provided a method of modeling a background signal when sequencing a polynucleotide strand using sequencing-by-synthesis, comprising: flowing a series of nucleotide flows onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; receiving output signals from the reactor array; and modeling a background signal for the loaded reaction confinement region using the received output signals and a model adapted to account at least for an exchange of ions between the one or more neighboring reaction confinement regions and a headspace adjacent the loaded reaction confinement region and the one or more neighboring reaction confinement regions.

According to an exemplary embodiment, there is provided a non-transitory machine-readable storage medium comprising instructions which, when executed by a processor, cause the processor to: receive output signals relating to chemical reactions resulting from the flow of a series of nucleotides onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; and determine a background signal for the loaded reaction confinement region using the received output signals and a model adapted to account at least for an exchange of ions between the one or more neighboring reaction confinement regions and a headspace adjacent the loaded reaction confinement region and the one or more neighboring reaction confinement regions.

According to an exemplary embodiment, there is provided a method of sequencing a polynucleotide strand, comprising: flowing a series of nucleotide flows onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; receiving output signals from the reactor array; and determining a background signal for the loaded reaction confinement region using the received output signals and a model of an output signal from the loaded reaction confinement region, the model adapted to account at least for a direct or indirect exchange of ions between the loaded reaction confinement region and the one or more neighboring reaction confinement regions.

Exemplary Embodiments

In various exemplary embodiments, one or more mathematical models may be used to process and/or analyze signal data from the sequencing of a template polynucleotide strand (e.g. by sequencing-by-synthesis).

In an exemplary embodiment, there is provided a method of sequencing a polynucleotide strand, comprising: (a) flowing a series of nucleotide flows onto a reactor array having multiple reaction confinement regions, one or more copies of the polynucleotide strand being located in a loaded reaction confinement region of the reactor array; (b) receiving output signals from the reactor array; (c) determining a background signal for the loaded reaction confinement region using a model of an output signal from the loaded reaction confinement region; (d) determining an incorporation signal from the loaded reaction confinement region using the model of an output signal from the loaded reaction confinement region; and (e) determining an estimate of a number of nucleotides incorporated into the polynucleotide strand.

In some cases, wherein the model comprises a function for a background signal component and a function for an incorporation signal component. In some cases, the step of determining the background signal comprises fitting the model to background signal data from the loaded reaction confinement region. In some cases, the background signal data comprises representative signal data for a first flow to the loaded reaction confinement region, and the first flow results in a non-incorporation event in the loaded reaction confinement region.

In some cases, the first flow is over a part of the polynucleotide strand that is known to be non-complementary to the nucleotide in the first flow. In some cases, the first flow is immediately preceded by a prior flow that contains the same nucleotide as in the first flow. In some cases, the step of determining the incorporation signal comprises fitting the model to signal data for a second flow to the loaded reaction confinement region to obtain the incorporation signal for the second flow. In some cases, the step of fitting the model to signal data for the second flow comprises applying greater weight to a portion of the signal data that is earlier or later in time than another portion of the signal data. In some cases, the function for the background signal component comprises a rate parameter relating to a rate of change in the amount of hydrogen ions in the loaded reaction confinement region. In some cases, the function for the background signal component further comprises a ratio parameter relating to a ratio of a rate of change in the amount of hydrogen ions in a representative empty reaction confinement region relative to the rate of change in the amount of hydrogen ions in the loaded reaction confinement region. In some cases, the ratio parameter is the rate of pH change in the representative empty reaction confinement region relative to the rate of pH change in the loaded reaction confinement region. In some cases, the ratio parameter is multiplied by the output signal from the representative empty reaction confinement region.

In some cases, the function for the background signal component comprises the difference between the output signal of a representative empty reaction confinement region and the output signal from the loaded reaction confinement region. In some cases, the function for the background signal component comprises the integral of the difference between the output signal of a representative empty reaction confinement region and the output signal from the loaded reaction confinement region from one or more prior time frames. In some cases, the function for the background signal component is derived from the flux of hydrogen ions between the nucleotide reagent of the first flow and the loaded reaction confinement region. In some cases, the function for the background signal component is further derived from the total flux of hydrogen ions in the loaded reaction confinement region. In some cases, the function for the background signal component is further derived from the flux of hydrogen ions between the nucleotide reagent of the first flow and the representative empty reaction confinement region.

In some cases, the function for the background signal component comprises an output signal from a representative empty reaction confinement region. In some cases, the representative empty reaction confinement region represents a plurality of empty reaction confinement regions within a region that includes the loaded reaction confinement region. In some cases, the fitting of the model for the first flow comprises varying at least one of the rate parameter and the ratio parameter to improve the fit to the signal data from the first flow. In some cases, the function for the incorporation signal component comprises a buffering parameter relating to the buffering capacity of the loaded reaction confinement region. In some cases, the fitting of the model to the signal data from the second flow comprises varying the buffering parameter to improve the fit with the signal data from the second flow.

In some cases, the reactor array includes a chemFET sensor array for detecting hydrogen ions in the reaction confinement region of the array. In some cases, the output signal is represented by the expression:

$$S_b = S_e R + \int \frac{S_e - S_b}{\tau_b} + \frac{1}{\beta_b} \int \varphi_i$$

wherein $S_b$ is the output signal from the loaded reaction confinement region, $S_e$ is the output signal from a representative empty reaction confinement region, R is $\tau_e/\tau_b$, $\tau_b$ is the time constant for the loaded reaction confinement region, $\tau_e$ is the time constant for the representative empty reaction confinement region, $\beta_b$ is the buffering capacity of the loaded reaction confinement region, and $\varphi_i$ is the flux of hydrogen ions generated by an incorporation reaction.

In some cases, the step of fitting the model to representative signal data for the first flow comprises setting the incorporation signal component to zero or near zero. In some cases, the step of determining an estimate of the number of nucleotides incorporated comprises applying an incorporation signal model to the incorporation signal. In some cases, the step of determining an estimate of the number of nucleotides incorporated further comprises fitting the incorporation signal model to the incorporation signal. In some cases, the step of determining an estimate of the number of nucleotides incorporated comprises comparing the incorporation signal to a set of reference incorporation signal curves.

In another exemplary embodiment, there is provided a sequencing apparatus comprising: a machine-readable memory; and a processor configured to execute machine-readable instructions, said instructions which when executed cause the apparatus to perform the above-mentioned methods. In another exemplary embodiment, there is provided a non-transitory machine-readable storage medium comprising instructions which, when executed by a processor, cause the processor to: (a) receiving output signals relating to chemical reactions resulting from the flow of a series of nucleotides onto a reactor array having multiple reaction confinement regions, one or more copies of the polynucleotide strand being located in a loaded reaction confinement region of the reactor array; (c) determine a background signal for the loaded reaction confinement region using a model of an output signal from the loaded reaction confinement region, wherein the model is stored in a computer memory; (d) determine an incorporation signal from the loaded reaction confinement region using the model of an output signal from the loaded reaction confinement region; and (e) determine an estimate of the number of nucleotides incorporated into the polynucleotide strand; (f) store the estimate of the number of nucleotides incorporated in the memory.

In another exemplary embodiment, there is provided a method of sequencing a polynucleotide strand, comprising: (a) flowing a nucleotide reagent onto a reactor array having multiple reaction confinement regions, one or more copies of the polynucleotide strand being located in a loaded reaction confinement region of the reactor array; (b) receiving signal data from the reactor array; (c) processing the signal data from the loaded reaction confinement region to obtain incorporation signal data; and (d) determining an estimate of a number of nucleotide incorporations resulting from the nucleotide reagent flow by applying an incorporation signal model to the incorporation signal data.

In some cases, the incorporation signal model comprises an equation for the flux of hydrogen ions generated by a nucleotide incorporation reaction. In some cases, the step of determining an estimate of the number of nucleotide incorporations comprises fitting the incorporation signal model to the incorporation signal data. In some cases, the step of fitting the incorporation signal model to the incorporation signal data comprises applying greater weight to a portion of the signal data that is earlier or later in time than another portion of the signal data. In some cases, the step of determining an estimate of the number of nucleotide incorporations further comprises using the results of the fitting to estimate the number of nucleotide incorporations. In some cases, the model further comprises an equation for a rate of change in the nucleotide amount in the loaded reaction confinement region.

In some cases, the rate of change in the nucleotide amount in the loaded reaction confinement region is expressed as being related to the rate of nucleotide diffusion into the reaction confinement region and the rate of nucleotide consumption by polymerase-catalyzed incorporation reactions. In some cases, the rate of nucleotide diffusion into the reaction confinement region is expressed as being proportional to the difference in the amount of nucleotide in the nucleotide reagent and the amount of nucleotide in the loaded reaction confinement region. In some cases, the rate of nucleotide consumption is expressed as being proportional to the amount of nucleotide in the loaded reaction confinement region multiplied by the amount of polymerase in the loaded reaction confinement region.

In some cases, the equation for the rate of change comprises a parameter relating to the diffusion rate of the nucleotide. In some cases, the equation for the rate of change comprises a parameter relating to the rate of polymerase activity. In some cases, the model further comprises an equation for the amount of active polymerase in the reaction confinement region. In some cases, the equation for the amount of active polymerase in the reaction confinement region comprises a parameter for the homopolymer n-mer length. In some cases, the fitting step results in an estimate of the homopolymer n-mer length. In some cases, the model further comprises an equation for the rate of change in the amount of active polymerase in the loaded reaction confinement region. In some cases, the rate of change is expressed as being related to the amount of nucleotide in the loaded reaction confinement region.

In some cases, the flux of hydrogen ions is expressed as being related to the number of active polymerases, as limited by the amount of nucleotide in the loaded reaction confinement region. In some cases, the flux of hydrogen ions is expressed as being proportional to the number of active polymerases multiplied by the amount of nucleotide in the loaded reaction confinement region. In some cases, the equation for the flux of hydrogen ions comprises a parameter relating to the rate of polymerase activity. In some cases, the model is a non-linear model.

In another exemplary embodiment, there is provided a sequencing apparatus comprising: a machine-readable memory; and a processor configured to execute machine-readable instructions, said instructions which when executed cause the apparatus to perform the above-mentioned methods. In another exemplary embodiment, there is provided a non-transitory machine-readable storage medium comprising instructions which, when executed by a processor, cause the processor to performed the above-mentioned methods.

In an exemplary embodiment, there is provided a method of analyzing signal data generated by sequencing of a polynucleotide strand using a pH-based method of detecting nucleotide incorporation(s). The incorporation of nucleotide bases into the template polynucleotide strand may be detected by measuring the amount of hydrogen ions released from the polymerase-catalyzed incorporation reactions. Additional details of pH-based sequence detection systems and methods can be found in commonly-assigned U.S. Patent Application Publication No. 2009/0127589 and No. 2009/0026082, which are both incorporated by reference herein in their entirety.

The sequencing reactions may be carried out on reactor arrays, such as those described in U.S. Patent Application Publication No. 2010/0300559, No. 2010/0197507, No. 2010/0301398, No. 2010/0300895, No. 2010/0137143, and No. 2009/0026082, which are all incorporated by reference herein in their entirety. A reactor array may have multiple reaction confinement regions for localizing a reaction of interest. An example of a reaction confinement region is a well for containing the reaction reagents and/or analytes. Another example of a reaction confinement region is a discrete region of a surface of the array that can bind or otherwise directly or indirectly confine the reagents and/or analytes in or on such discrete region. As used herein, the terms "well" and "microwell" are to be considered interchangeable with the term "reaction confinement region." The template polynucleotide strand can be confined to the reaction confinement region in various ways. For example, the template polynucleotide strand can be attached to a substrate particle (e.g. bead, microparticle, or other substrate moiety that fits inside wells of a reactor array, or is directly or indirectly coupled to a surface of the reactor array). The particle may contain multiple identical copies (e.g. clonal) of the template polynucleotide strand.

The reaction confinement regions of the reactor array can be associated with sensors that detect hydrogen ions and produce an output signal (e.g. a change in voltage level or current level) based on the amount of hydrogen ions and/or changes thereof. In an exemplary embodiment, the sensor may be a pH sensor. The sensor may be a chemFET (chemical field-effect transistor) sensor that detects hydrogen ions to measure pH. The amplitude of the signals from the chemFET sensors may be related to the amount of hydrogen ions detected.

FIGS. 1A and 1B show an example of how the flow of a nucleotide reagent solution over a reactor array generates a signal. FIG. 1A shows a cross-sectional view of a portion 206 of a flow chamber on a flow cell 200. A nucleotide reagent solution is flowed (shown by arrow 208) over the microwells 202 of the reactor array. In this example, the array of microwells 202 is integrated with a sensor array 205 for detecting hydrogen ions. A reference electrode 204 is fluidly connected to flow cell 200.

FIG. 1B shows a close-up view of a microwell 201 of the reactor array. The microwell 201 contains a bead 212 that holds multiple identical copies of a template polynucleotide strand. Beneath the microwell 201 there is a chemFET sensor 214 for detecting hydrogen ions (and thus acting as a pH sensor) in the microwell 201 and generating an output signal. Sensor 214 includes a floating gate 218 having sensor plate 220 separated from the microwell interior by passivation layer 216. Sensor 214 is responsive to (and generates an output signal related to) the amount of charge 224 present on the passivation layer 216 opposite of sensor plate 220. Changes in charge 224 cause changes in the current between source 221 and drain 222 of the chemFET, which generates an output signal for the sensor 214.

The nucleotide solution moves into the microwell 201 by diffusion 240. If the nucleotide is complementary to the next base on the polynucleotide strand, then polymerase-catalyzed reactions with the polynucleotide strands on the bead 212 generate hydrogen ions that affect the amount of charge adjacent to sensor plate 220. The output signals from the sensors are collected and processed to estimate the number of nucleotides incorporated into the polynucleotide strand. With each successive flow of the nucleotide reagent, the output signal from the sensors may be collected over a time interval (e.g. in a continuous or intermittent manner).

A signal of interest in this example is the signal produced by the polymerase reaction-generated hydrogen ions. However, in addition to this signal of interest, there is also a background component of the measured output signal that results from other sources of pH changes. Since the bulk reagent solution used for the nucleotide flow also contains hydrogen ions, one of the sources of pH change in the wells is the diffusion of hydrogen ions from the bulk solution into the well as successive nucleotide reagent flows are passed over the reactor array (i.e. reagent change noise).

FIGS. 2A and 2B show how the measured output signal may compare to the background signal component. FIG. 2A shows three output signals from a chemFET microwell containing a particle with a template polynucleotide strand attached. Curve 606 plots the signal from the microwell during a wash step. Curve 600 plots the measured output signal from the microwell for a flow that results in a single nucleotide incorporation into the polynucleotide strand. Curve 602 plots the measured output signal from the microwell for a different flow that results in no nucleotide incorporation. Region 604 is the difference between the two output signals (600 and 602) that is due to the generation of hydrogen ions by the nucleotide incorporation reaction. In FIG. 2B, curve 608 is the difference between the values of curves 600 and 602, and is the part of the raw output signal of curve 600 which results from hydrogen ions produced in the nucleotide incorporation reaction, i.e. the incorporation signal of interest.

In an exemplary embodiment, there is provided a model for the measured output signal from the well of a reactor array. The output signal may be modeled as a linear combination of one or more signal components. For example, the output signal may be modeled as a linear combination of a function for the background signal component and a function for the incorporation signal component. The output signal model may also include other sources of errors or offsets (e.g. signal gain). For example, the output signal may be represented as $x(t)=I(t)+B(t)+e$, where $x(t)$ is the output signal over time "t", $I(t)$ is a function for the incorporation signal component, $B(t)$ is a function for the background signal component, and "e" is a corrective parameter to account for error, offsets, or other compensatory correction.

As explained above, one of the sources of the background signal in the output signal is the pH changes resulting from the nucleotide reagent solution (i.e. bulk solution) that is passed over the reactor array. The pH changes in the well can be affected by the buffering capacity of the well. For example, the walls of the well, the substrate particle, the polynucleotide strands, and/or the polymerase enzymes may buffer the pH changes. The pH change may also be affected by the diffusion of hydrogen ions into and out of the well. One or more of these effects can be mathematically modeled to predict the background signal in the well.

In an exemplary embodiment, the background signal component may be a function of the output signal from a representative empty well. Having multiple wells, the reactor array may have some wells that contain the substrate particles (e.g. beads) and other wells that are empty. The substrate particles may be dispersed randomly in the wells of the array. For example, the substrate particles may be flowed in a fluid onto the reactor array where they settle randomly into the wells. As a result, some wells may contain the particles whereas other wells may be empty. For example, FIG. 3 shows a random distribution of beads in a portion of a reactor array 500 having empty microwells 501 and loaded microwells 502.

FIG. 4 shows an example of the flux of hydrogen ions into a loaded well compared to an empty well. Two neighboring microwells, 631 and 641, are shown at four different times: before the next nucleotide reagent is introduced ($t_0$), immediately after the nucleotide reagent is flowed to the microwells ($t_1$), during equilibration of the nucleotide reagent with the microwell contents ($t_2$), and after equilibrium has been achieved ($t_3$). The change in sensor signal due to the reagent change can be described using a two compartment model, in which one compartment is the flow of nucleotide (shown by the horizontal arrow) in region 638 adjacent to the opening of a microwell and the other compartment is the surface 640 at the bottom of a microwell adjacent to the sensor.

As shown in FIG. 4, $S_T$ represents a measured signal at the top of the well (i.e. from the bulk nucleotide solution); $S_b$ represents a measured signal from the loaded well; and $S_e$ represents a measured signal from the empty well. With the flow of new nucleotide solution 630, there is a concentration difference 636 between the two compartments. This concentration difference results in a flux of hydrogen ions into the microwells. There may also be a flux of hydrogen ions out of the well. The net flux of hydrogen ions in/out of the loaded microwell is represented as $\varphi_b$ (632) and the net flux of hydrogen ions in/out of the empty microwell is represented as $\varphi_e$ (634). In the loaded microwell, hydrogen ions are generated by the reaction, which adds to the flux.

The flux of hydrogen ions described above can be modeled by a set of reaction-diffusion equations. The function for the background signal component can be derived from one or more equations that describe the diffusion of hydrogen ions into the well (loaded and/or empty). For example, the background signal function may be derived from an equation for the flux of hydrogen ions into the well (loaded and/or empty) as being proportional to the difference between the amount of hydrogen ions in the nucleotide reagent and the amount of hydrogen ions in the well (loaded and/or empty). In another example, the background signal function may be derived from an equation for the total flux of hydrogen ions in the well (loaded and/or empty) as being proportional to the rate of change of the measured output signal. The equations used to derive the background signal function may have a parameter relating to the rate of hydrogen ion diffusion in the solution for the well (loaded and/or empty) and/or a parameter relating to the buffering capacity of the well (loaded and/or empty).

As used herein, the term "relating to" between two quantity terms means that the two quantity terms have a mathematical relationship. For example, one quantity term may be proportional or equal to the other quantity term. In another example, one quantity term may be derived from or result from the application of a transformation function on the other quantity term. According to an exemplary embodiment, the amount of some element may be represented by any suitable manner to quantify the element. For example, the amount of the element may be represented as concentration, absolute number, relative number, detectable activity, or any other manner of quantifying the element. For example, hydrogen ions may be represented as the concentration of hydrogen ions (also conventionally measured as pH) or the signal level corresponding to the hydrogen ion concentration (e.g. signal counts). Computations for solving the models used in the present invention may involve finding exact solutions or using numerical analysis for approximate solutions. Likewise, function terms (e.g. integrals) used herein may be substituted with terms that are approximations thereof.

The function for the background signal component may include one or more parameters. Such parameters may include a parameter relating to the rate of change in the amount of hydrogen ions (e.g. rate of pH change) in the loaded and/or empty well (e.g. a time constant for the well); a parameter relating to the ratio of the preceding rate of change parameters (e.g. rate of change in a representative empty well divided by rate of change in the loaded well); and/or a parameter relating to the buffering capacity of the loaded and/or empty well. The function for the incorporation signal may include a buffering parameter relating to the buffering capacity of the well (loaded and/or empty).

An example of a set of reaction-diffusion equations for constructing a model of the output signal according to an exemplary embodiment is shown in Equations 1-12 as follows. Equation 1 below expresses the flux of hydrogen ions from the bulk solution into the loaded well as being proportional to the difference in the hydrogen ion concentration between the bulk solution ($S_T$) and the well ($S_b$). Equation 2 below expresses the total flux of hydrogen ions in the loaded well $\varphi_b + \varphi_i$, with pi being the flux of hydrogen ions generated by the nucleotide incorporation reaction) as being proportional to the rate of change of the measured signal $S_b$. The parameter $\alpha_b$ is a diffusion constant of the hydrogen ions in the loaded well, and the parameter $\beta_b$ is a constant that reflects the buffering capacity of the loaded microwell, including the buffering provided by the microwell wall, the substrate particle, the polynucleotide strands, and/or the polymerase enzymes.

$$\frac{S_T - S_b}{\alpha_b} = \varphi_b \qquad \text{Eqn. 1}$$

$$\varphi_b + \varphi_i = \frac{\delta S_b}{\delta t} \beta_b \qquad \text{Eqn. 2}$$

Equation 3 below is derived by manipulation and rearranging of the terms in Equations 1 and 2.

$$\frac{S_T - S_b}{\alpha_b} + \varphi_i = \frac{\delta S_b}{\delta t} \beta_b \qquad \text{Eqn. 3}$$

Equation 4 below is derived by manipulation and rearranging of the terms in Equation 3. Equation 5 below is obtained by having $\tau_b = \alpha_b \beta_b$ as the time constant for the loaded well relating to the rate at which the pH in the well approaches the pH in the bulk solution.

$$S_T - S_b = \frac{\delta S_b}{\delta t} \alpha_b \beta_b - \alpha_b \varphi_i \qquad \text{Eqn. 4}$$

$$S_T - S_b = \frac{\delta S_b}{\delta t} \tau_b - \alpha_b \varphi_i \qquad \text{Eqn. 5}$$

Like Equation 1, Equation 6 below expresses the flux of hydrogen ions from the bulk solution into the representative empty well as being proportional to the difference in hydrogen ion concentration between the bulk solution ($S_T$) and the well ($S_e$). Equation 6 also expresses the flux of hydrogen ions as being proportional to the rate of change of the measured signal $S_e$. The parameter ae is a diffusion constant of the hydrogen ions in the empty well, and the parameter $\beta_e$ is a constant that reflects the buffering capacity of the empty microwell caused by the microwell wall and the solution within the empty well. Because the empty well does not contain a polynucleotide strand or bead, there is no need to consider hydrogen ions generated by incorporation reactions, and there is no buffering from the substrate particle, polynucleotide strands, or polymerase enzymes.

$$\frac{S_T - S_e}{\alpha_e} = \varphi_e = \frac{\delta S_e}{\delta t} \beta_e \qquad \text{Eqn. 6}$$

Equation 7 below is derived by manipulation and rearranging of the terms in Equation 6. Equation 8 below is obtained by having $\tau_e = \alpha_e \beta_e$ as the time constant of the well that relates to the rate at which the pH in the well approaches the pH of the bulk solution.

$$S_T - S_e = \frac{\delta S_e}{\delta t} \alpha_e \beta_e \qquad \text{Eqn. 7}$$

$$S_T - S_e = \frac{\delta S_e}{\delta t} \tau_e \qquad \text{Eqn. 8}$$

Equation 8 is combined with Equation 5 to arrive at Equation 9 below.

$$\frac{\delta S_e}{\delta t}\tau_e + S_e - S_b = \frac{\delta S_b}{\delta t}\tau_b - \alpha_b \varphi_i \qquad \text{Eqn. 9}$$

Equation 10 below is derived by manipulation and rearranging of the terms in Equation 9, and integration of the differentials yields the following relationship between $S_b$ and $S_e$.

$$S_b = S_e \frac{\tau_e}{\tau_b} + \int \frac{S_e - S_b}{\tau_b} + \frac{1}{\beta_b}\int \varphi_i \qquad \text{Eqn. 10}$$

Equation 11 below is obtained by having $R = \tau_e/\tau_b$.

$$S_b = S_e R + \int \frac{S_e - S_b}{\tau_b} + \frac{1}{\beta_b}\int \varphi_i \qquad \text{Eqn. 11}$$

In Equation 11, the first two terms represent the background signal component and the third term represents the incorporation signal component. Equation 11 may be numerically approximated using any suitable numerical technique. For example, a numerical approximation of Equation 11 is given by Equation 12 below, where $\Delta t$ is the time-step used in the numerical solution, for a given time frame "j":

$$S_{bj} = \frac{\left\{ S_{ej}R + \dfrac{\sum_{i=0}^{j-1} S_{ei} - S_{bi}}{\tau_b} + \dfrac{1}{\beta_b}\int \varphi_i \right\}}{\left(1 + \dfrac{\Delta t}{\tau_b}\right)} \qquad \text{Eqn. 12}$$

In some cases, it may be useful to express Equation 12 in an alternate form, as in Equation 13 below.

$$S_b - S_e = S_e(R-1) + \int \frac{S_e - S_b}{\tau_b} + \frac{1}{\beta_b}\int \varphi_i \qquad \text{Eqn. 13}$$

An example numerical approximation of Equation 13 is given by Equation 14 below:

$$S_{bj} - S_{ej} = \frac{\left\{ S_{ej}(R-1) + \dfrac{\sum_{i=0}^{j-1} S_{ei} - S_{bi}}{\tau_b} + \dfrac{1}{\beta_b}\int \varphi_i \right\}}{\left(1 + \dfrac{\Delta t}{\tau_b}\right)} \qquad \text{Eqn. 14}$$

As demonstrated here, in the mathematical model, the background signal may be a function of the output signal from a representative empty well on the reactor array. The empty well here is identified as a representative empty well because the signal data may be from a single empty well or an estimate from multiple empty wells as representative of an empty well. The signal data from multiple empty wells may be subject to any suitable statistical analysis to obtain a single value as a representative estimate that quantitatively summarizes the collection of signal data, including calculating an average, a weighted average, some function of the average, a mean, a mode, or applying some other transformation function to the signal data.

Figure 5B:
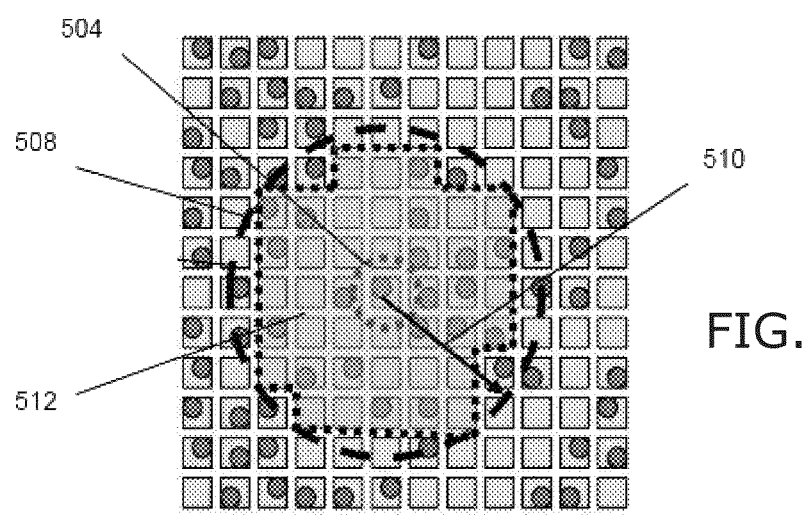

In cases where multiple empty wells are used, the empty wells may be in a region of the reactor array that includes the loaded well of interest (e.g. empty wells in a neighborhood around the well of interest). FIGS. 5A and 5B show examples of how regions for selecting empty wells can be defined. FIG. 5A shows a loaded well of interest 504 and a region 506 defined by a 7×7 square 505 of microwells. The size of the region may vary and may be selected on the basis of various factors, such as the relative number of loaded wells and its burden on computation time. In another example, FIG. 5B shows a region 512 defined by a circle 508 having a radius 510 from the microwell of interest 504. Not all of the empty well signals in a given region need be used. In some circumstances, it may be advantageous to minimize the number of empty well output signals being used in order to minimize computation time. For example, a random selection of available empty wells within a region may be used.

According to an exemplary embodiment, the background component of the output signal model may be established by fitting the model to representative signal data from a well that results in a non-incorporation event, with the incorporation signal component of the model being set to zero or substantially zero. In this context, the term "non-incorporation" means that the nucleotide flow does not result in any significant incorporation reactions (also referred to herein as a "0-mer flow"). However, there may be non-significant incorporation reactions due to errors such as phase loss effects or misincorporations.

The signal data from the non-incorporation flow is identified as representative signal data because it can be signal data from a single 0-mer flow or from multiple 0-mer flows. The signal data from multiple 0-mer flows may be subject to any suitable statistical analysis to obtain a single value as a representative estimate that quantitatively summarizes the collection of signal data, including calculating an average, a weighted average, some function of the average, a mean, a mode, or applying some other transformation function to the signal data. Where multiple 0-mer flows are used, the fitting may be applied to each 0-mer flow individually to obtain a representative estimate (e.g. by taking the average of the fitting results), or the fitting may be applied to the multiple 0-mer flows simultaneously (e.g. the fitting may be applied to many 0-mer flows to find the best fit to the entire set of 0-mer flows) to obtain the representative estimate, or the fitting may be applied to the multiple 0-mer flows collectively (e.g. an average of the signal data from multiple 0-mer flows) to obtain the representative estimate.

The non-incorporation signal can be obtained by any suitable manner. For example, the non-incorporation flows may be those over known base sequences (e.g. the key sequence or other initial part of the polynucleotide sequence) that are expected to produce non-incorporation events because they are non-complementary to the nucleotide being flowed. In another example, the non-incorporation signal can be produced by immediately repeating the same nucleotide flow (e.g. double tapping). Since the complementary nucleotides would have already incorporated in the prior flow, the subsequent flow of the same nucleotide (i.e. without an intervening flow of a different nucleotide) would not be expected to result in any further nucleotide incorporations.

The background signal fitting may establish one or more parameters of the background component of the signal model. For example, the fitting may involve finding the parameters $\tau_b$ and/or R in the model to improve (e.g. optimize) the model fit to the measured signal data. Any suitable fitting technique can be used to fit the model to the measured signal data, such as regression analysis or Bayesian techniques. The fitting may involve an iterative process of varying the $\tau_b$ and R parameters to improve the fit (e.g. obtaining the best fit by minimizing the residual error sums) between the model-predicted signals and the measured signal data. For example, the fitting may involve a least squares analysis of the model-predicted signals and a Levenberg-Marquardt algorithm applied to find a best-fitting solution.

The fitting can encompass any suitable portion of the signal data for the flow. In some cases, the fitting may be applied to selected portions of the signal data. For example, the fitting may be applied to portions of the signal data containing relatively more information about the relevant characteristics of the signal. In some cases, the fitting may apply greater weight to certain portions of the signal data than others. For example, signal data from earlier time frames in the nucleotide flow may be more important than those at later time frames in the flow. In such cases, one or more data points at an earlier time frame may be given greater weight than one or more data points at a later time frame in the fitting process.

In some cases, the parameter(s) of the background signal component may drift as the sequencing operation progresses to later nucleotide flows. This effect may be due to a change in the buffering capabilities of the loaded well, nucleotide reagent, and/or wash solution. The buffering capacity of the loaded well may change due to various effects, such as the loss of polymerase enzymes and/or conversion of single-stranded DNA to double-stranded DNA. The buffering capacity of the nucleotide reagent and wash solution may change due to changes in the concentration of the buffering species (e.g. an increase in dissolved $CO_2$) and/or changes in the composition of the wash solution. In such cases, the parameter(s) may be adjusted to account for this drift. For example, the parameter $\tau_b$ may drift downward and the parameter R may drift upward with later flows in the sequencing operation as polymerase enzymes are lost from the loaded well. As such, the value of parameter $\tau_b$ may be adjusted downward for one or more later flows. Also, the value of parameter R may be adjusted upward for one or more later flows.

Having established the background component of the output signal model (e.g. by fixing one or more parameters of the function for the background component), the output signal model can then be fitted to signal data from other flows in the well, including those that result in incorporation events. For example, the background component can be obtained from 0-mer flows in one or more of the earlier flows in the sequencing operation (e.g. flows over the known key sequence of the polynucleotide strand), and then with the background signal component established, the output signal model can be applied to flows that occur later in the sequencing operation (e.g. for unknown portions of the polynucleotide sequence).

This fitting of the output signal model may establish one or more parameters of the incorporation signal component of the signal model. For example, the fitting may involve finding the parameter $\beta_b$ in the model to improve (e.g. optimize) the model fit to the measured signal data. As explained above, any suitable fitting technique can be used. Also as explained above, this fitting of the output signal model can encompass any suitable portion of the output signal data. These fitted parameter(s) can then be used to calculate the incorporation signal, which can be further analyzed to estimate the number of nucleotides incorporated into the polynucleotide strand.

Figure 6A:
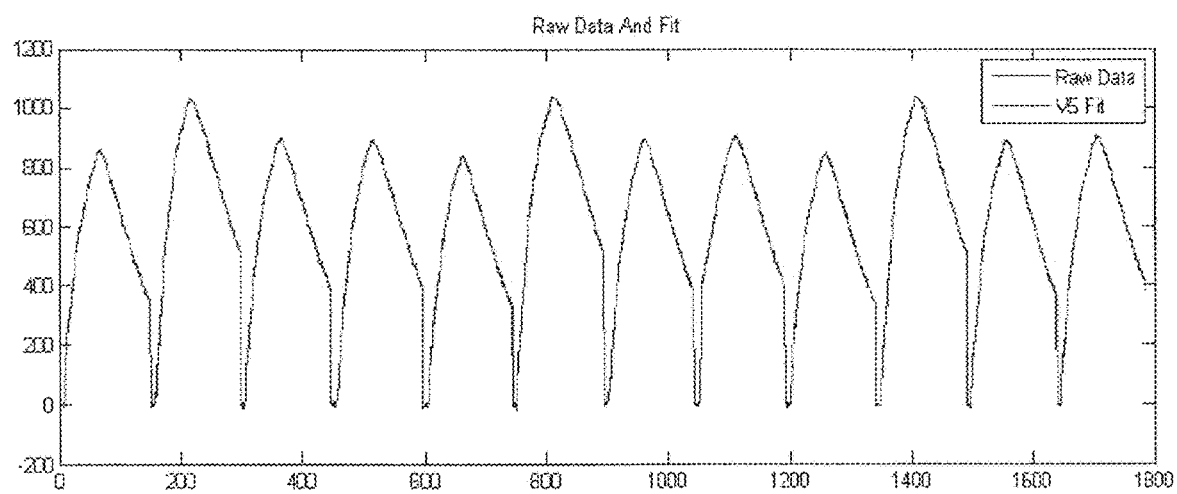
FIGS. 6A and 6B show an example of measured signals and data according to an exemplary embodiment.
Figure 6B:
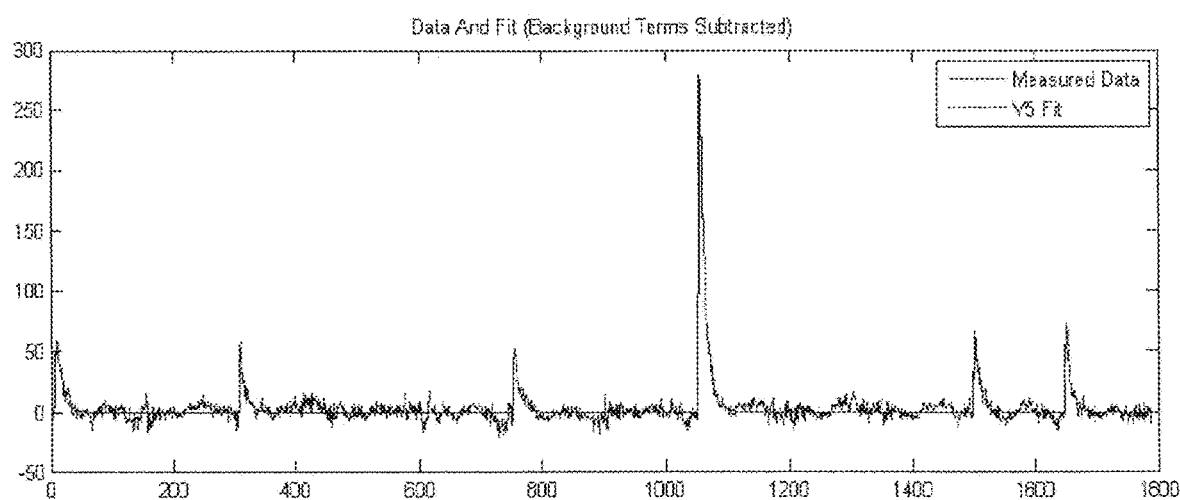

FIGS. 6A and 6B show an example of measured signals and data according to an exemplary embodiment. FIG. 6A shows the measured output signal ("Raw Data") from a well over multiple flows. The model-predicted signal curve ("V5 fit") is superimposed on the measured output signal curve (mostly overlapping). FIG. 6B shows the incorporation signal curve (noisy plot line; "Measured Data") that is derived by subtracting the background signal from the output signal in comparison to the incorporation signal curve (straight line; "V5 Fit") derived from solving the output signal model (the two plot lines are overlapping).

Figure 12A:
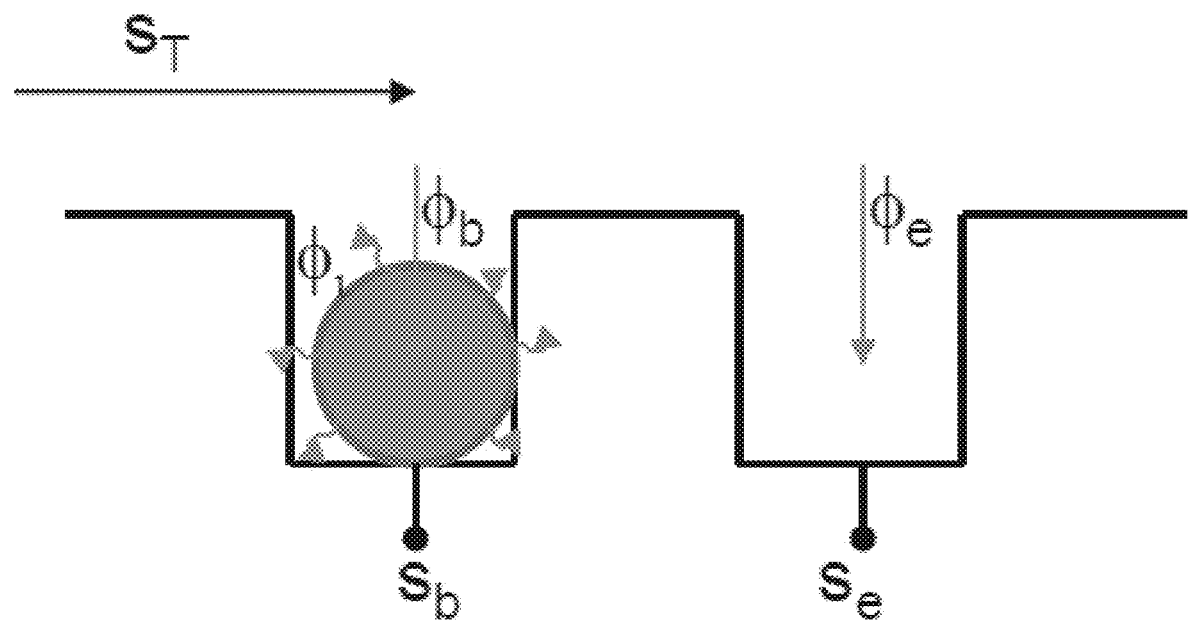
FIG. 12A shows an example of background model according to an exemplary embodiment.

FIG. 12A shows an example of background model according to an exemplary embodiment. This background model takes into account transport of hydrogen ions between empty wells and bead-containing wells and a common 'bulk' concentration above all the wells. The figure shows changing pH background above the wells. In the figure, $S_T$ represents a measured signal at the top of the well (from the bulk nucleotide solution); $S_b$ represents a measured signal from the loaded well; and $S_e$ represents a measured signal from the empty well. With the flow of a new nucleotide solution, there is a concentration difference between the two compartments, which results in a flux of hydrogen ions into the microwells. There may also be a flux of hydrogen ions out of the well. The net flux of hydrogen ions in/out of the loaded microwell is represented as $\varphi_b$ and the net flux of hydrogen ions in/out of the empty microwell is represented as $\varphi_e$. The flux of hydrogen ions generated by the nucleotide incorporation reaction in the loaded microwell is represented as $\varphi_i$.

Figure 12B:
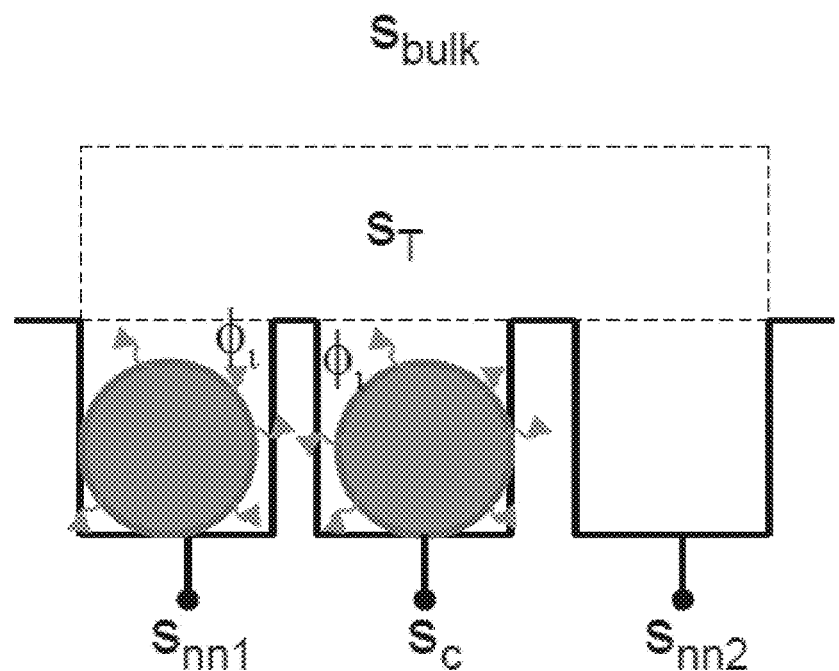
FIG. 12B shows an example of a nearest-neighbor background model according to an exemplary embodiment.

FIG. 12B shows an example of a nearest-neighbor background model according to an exemplary embodiment. This nearest-neighbor background model is an extension of a background model such as in FIG. 12A that includes one or more effects of one or more neighboring wells (which may or may not be generating protons). The figure shows neighboring wells while changing pH "bulk" above the wells. Although two neighbors are shown, the model may be developed for more neighbors (including, e.g., a hexagonally-packed array with effects from the six nearest neighbors). More generally, in some cases, the model may include at least two, at least three, at least four, at least five, at least six, or more, neighboring wells. In the figure, $S_{nm1}$ and $S_{nm2}$ represent the proton concentration in two exemplary nearest neighbors; $S_c$ represents the proton concentration in the well in the center of the two exemplary nearest neighbors; $S_T$ represents the proton concentration in the headspace above the local group of wells; and $S_{bulk}$ represents the proton concentration in the bulk fluid.

Figure 12C:
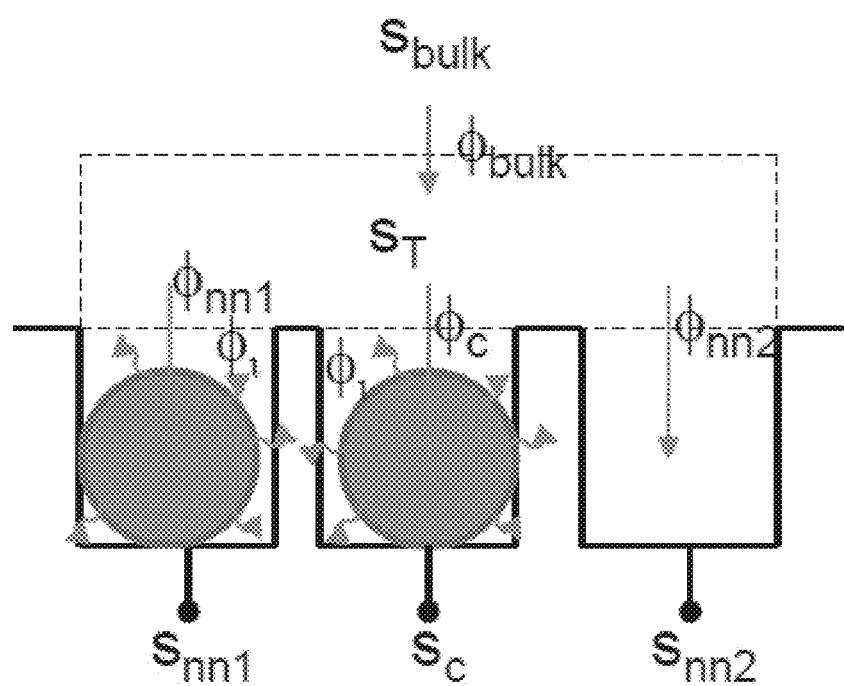
FIG. 12C shows an example of a nearest-neighbor background model according to an exemplary embodiment.

FIG. 12C shows an example of a nearest-neighbor background model according to an exemplary embodiment. The figure shows neighboring wells while changing pH "bulk" above the wells. Although two neighbors are shown, the model may be developed for more neighbors (including, e.g., a hexagonally-packed array with effects from the six nearest neighbors). More generally, in some cases, the model may include at least two, at least three, at least four, at least five, at least six, or more, neighboring wells. In the figure, $S_{nm1}$ and $S_{nm2}$ represent the proton concentration in two exemplary nearest neighbors; $S_c$ represents the proton concentration in the well in the center of the two exemplary nearest neighbors; $S_T$ represents the proton concentration in the headspace above the local group of wells; and $S_{bulk}$ represents the proton concentration in the bulk fluid. The net flux of hydrogen ions in/out of the two exemplary nearest neighbors is represented as $\varphi_{nm1}$ and $\varphi_{nm2}$, respectively. The net flux of hydrogen ions in/out of the headspace is represented as $\varphi_{bulk}$.

In an exemplary embodiment, the local neighborhood of wells may be assumed to exchange protons with a 'headspace' directly above the local group. In an exemplary embodiment, the headspace may exchange protons with the bulk fluid. In some cases, the proton concentration in the bulk fluid may be assumed to be constant over a wide area (e.g., ~50 well dimensions). In an exemplary embodiment, a background model may be derived by considering the conservation of protons in the headspace, which yields the following characteristic equation:

$$\sum_{nn=1}^{N_{nn}} \frac{(s_{nn} - s_T)}{\alpha_w} + \frac{s_{bulk} - s_T}{\alpha_{bulk}} + \frac{s_c - s_T}{\alpha_w} = \beta_T \frac{ds_T}{dt} \qquad \text{Eqn. NN1}$$

where $S_{nm}$ represents the proton concentration in each of a set of nearest neighbors (e.g., each of 6 neighbors in a hexagonally-packed array); $S_c$ represents the proton concentration in the well in the center of the nearest neighbors; $S_T$ represents the proton concentration in the headspace above the local group of wells (e.g., the well in the center and its nearest neighbors); $S_{bulk}$ represents the proton concentration in the bulk fluid; $\alpha_w$ represents the resistance to proton movement between individual wells and the headspace; $\alpha_{bulk}$ represents the resistance to proton movement between the headspace and the bulk fluid; $\beta_T$ represents the buffer capacity of the headspace; and $N_{nn}$ represents the number of nearest neighbors in the set (e.g., 2, 3, 4, 5, or more neighbors, such as 6 neighbors for an hexagonally-packed array).

Equation NN1 may be rearranged to yield:

$$\sum_{nn=1}^{N_{nn}} \frac{s_{nn}}{\alpha_w} + \frac{s_{bulk}}{\alpha_{bulk}} + \frac{s_c}{\alpha_w} = \beta_T \frac{ds_T}{dt} + \left(\frac{N_{nn}+1}{\alpha_w} + \frac{1}{\alpha_{bulk}}\right) s_T. \qquad \text{Eqn. NN2}$$

Then, considering the conservation of protons in the central well yields the following characteristic equation:

$$\frac{s_T - s_c}{\alpha_w} + \phi_i = \beta_c \frac{ds_c}{dt} \qquad \text{Eqn. NN3a}$$

where $\varphi_i$ represents the flux of hydrogen ions generated by the nucleotide incorporation reaction and $\beta_c$ is a constant that reflects the buffering capacity of the central well, which may then be rearranged to yield:

$$s_T = s_c - \alpha_w \phi_i + \alpha_w \beta_c \frac{ds_c}{dt} \qquad \text{Eqn. NN3b}$$

which may be differentiated to yield:

$$\frac{ds_T}{dt} = \frac{ds_c}{dt} - \alpha_w \frac{d\phi_i}{dt} + \alpha_w \beta_c \frac{d^2 s_c}{dt^2}. \qquad \text{Eqn. NN4}$$

Equations NN3b and NN4 may then be substituted into the headspace equation NN2 to eliminate the unknown $S_T$ and obtain:

$$\sum_{nn=1}^{N_{nn}} \frac{s_{nn}}{\alpha_w} + \frac{s_{bulk}}{\alpha_{bulk}} + \frac{s_c}{\alpha_w} - \beta_T \left(\frac{ds_c}{dt} - \alpha_w \frac{d\phi_i}{dt} + \alpha_w \beta_t \frac{d^2 s_c}{dt^2}\right) +$$

$$\left(\frac{N_{nn}+1}{\alpha_w} + \frac{1}{\alpha_{bulk}}\right)\left(s_c - \alpha_w \phi_i + \alpha_w \beta_c \frac{ds_c}{dt}\right)$$

Then, defining $\gamma = (N_{nn} + 1 + \alpha_w/\alpha_{bulk})$, $\tau_c = \alpha_w \beta_c$, and $\tau_T = \alpha_w/\beta_T$, and collecting like terms and re-arranging yields:

$$\sum_{nn=1}^{N_{nn}} s_{nn} + \frac{\alpha_w s_{bulk}}{\alpha_{bulk}} = \qquad \text{Eqn. NN5}$$

$$(\gamma - 1) s_c + (\tau_T + \gamma \tau_c) \frac{ds_c}{dt} + \tau_T \tau_c \frac{d^2 s_c}{dt^2} - \alpha_w \gamma \phi_i - \alpha_w \tau_\gamma \frac{d\phi_i}{dt}.$$

Equation NN5 describes the relationship between the central well in a local group, the nearest neighbors to that well, and the bulk fluid, all interacting with each other through the headspace above the local group. The same equation (without the incorporation flux terms) describes the behavior of the local group around an empty well:

$$\sum_{nn=1}^{N_{nn}} s_{nn} + \frac{\alpha_w s_{bulk}}{\alpha_{bulk}} = (\gamma - 1) s_c + (\tau_T + \gamma \tau_c) \frac{ds_c}{dt} + \tau_T \tau_c \frac{d^2 s_c}{dt^2}.$$

Equation NN5 may then be combined with the empty well equation to eliminate the unknown $S_{bulk}$ to provide a complete form of an exemplary nearest-neighbor background model:

$$\sum_{nn=1}^{N_{nn}} \left(s_{nn-e} - s_{nn-e}\right) + (\gamma - 1) s_e + (\tau_T + \gamma \tau_e) \frac{ds_e}{dt} + \gamma \tau_e \frac{d^2 s_e}{dt^2} =$$

$$(\gamma - 1) s_e + (\tau_r + \gamma \tau_e) \frac{ds_e}{dt} + \tau_r \tau_c \frac{d^2 s_e}{dt^2} - \alpha_w \gamma \phi_i - \alpha_w \tau_T \frac{d\phi_i}{dt}$$

In an exemplary embodiment, the nearest-neighbor background model may be simplified in one or more ways. In an exemplary embodiment, for practical purposes, $\tau_T$ may be deemed to be likely small since the buffer capacity of the headspace is small. As a result, the second derivative terms may be deemed relatively insignificant, and the model may then be simplified to obtain:

$$\sum_{nn=1}^{N_{nn}} \left(s_{nn-e} - s_{nn-e}\right) + (\gamma - 1) s_e + \gamma \tau_e \frac{ds_e}{dt} =$$

$$(\gamma - 1) s_e + \gamma \tau_e \frac{ds_e}{dt} - \alpha_w \gamma \phi_i - \alpha_w \tau_T \frac{d\phi_i}{dt}.$$

Finally, integrating and re-arranging yields:

Eqn. NN6

$$s_c = Rs_e + \frac{(\gamma-1)}{\gamma\tau_c}\int s_e - s_c + \frac{\int \sum_{nn=1}^{N_{nn}}(s_{nn-c} - s_{nn-e})}{\gamma\tau_c} + \frac{1}{\beta_c}\int \phi_I + \frac{\tau_T}{\gamma\beta_c}\phi_1$$

where $R=\tau_e/\tau_c$, $\tau_e=\alpha_e\beta_e$, and $\tau_c=\alpha_c\beta_c$. The parameter gamma is a unitless constant that indicates the sensitivity of the headspace to the effects of neighboring wells. Very large values of gamma cause the nearest-neighbor extension model to revert to a basic background model that is not extended to nearest neighbors.

In Equation NN6, the nearest-neighbor term (which is the term with the summation over neighbors within an integral) compensates for cross-talk of neighboring wells beyond what the empty wells experience. In an embodiment, the final flux term (which is the last term on the right) can probably be neglected because it is scaled by $\tau_T/\gamma$. The effective time constant of the well (see the coefficient prior to first integral) in the nearest-neighbor extension model is slightly different than in the basic background model. In an embodiment, the parameter gamma may be roughly estimated from geometry as follows:

$$\gamma = \left(N_{nn} + 1 + \frac{\alpha_w}{\alpha_{bulk}}\right)$$

In an embodiment, the neighbors are hexagonally-arranged and $N_{nn}$ is 6. In an embodiment, the effective cross section of individual wells is about $1/7^{th}$ that of the effective cross section between the headspace and the bulk, so the ratio $\alpha_w/\alpha_{bulk}$ might then be about 7, and gamma might then be approximately 14, if the system really behaves as described and diffusion dominates in the headspace region.

Figure 13:
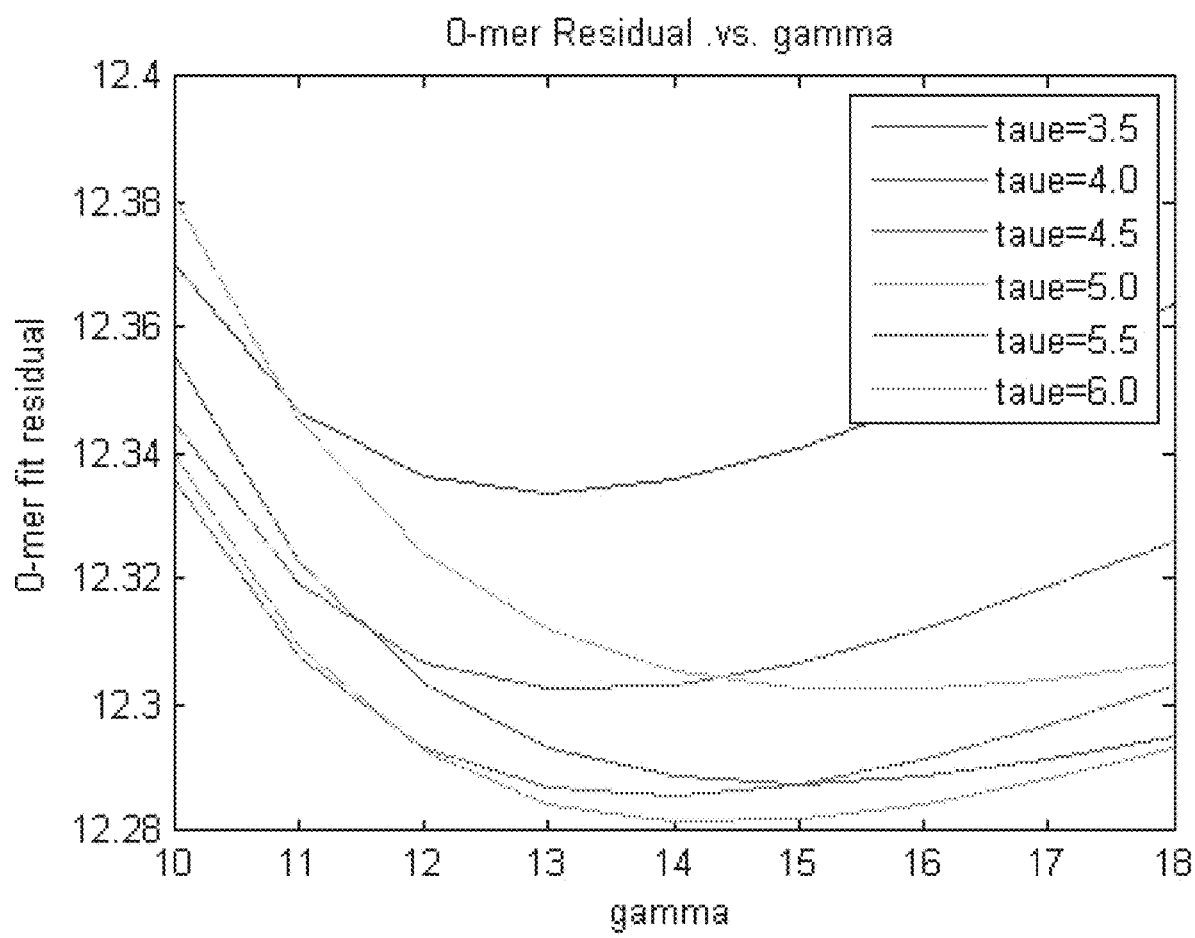
FIG. 13 shows test data for an example of a nearest-neighbor background model according to an exemplary embodiment.

FIG. 13 shows test data for an example of a nearest-neighbor background model according to an exemplary embodiment. Shown are data for a 50×50 region of VEG-96. The nearest-neighbor-background model was fit to all wells, in key flows. High-confidence 0-mers were identified in non-key flows. The model was refit to all good 0-mer flows for each well. Here, the model has three independent parameters. In an embodiment, R was fit per well. In an embodiment, $\tau_e$ and gamma were grid-searched to find a value that produced the minimum mean squared error in all 0-mer flows across all wells. In an embodiment, $\tau_e$=5.0 and gamma=14 produced the minimum error fit across all wells/0-mer flows. The geometric estimate for gamma produces the minimum fit error.

Although the exemplary embodiments of nearest-neighbor background models are discussed in the context of wells, they are not so limited and they more generally apply to any arrangement of reaction confinement regions or areas. For example, the arrangement could include a group of wells configured to contain beads to which one or more templates are attached, or wells that can otherwise confine templates without any use of beads or other particles (such as by direct or indirect binding to a surface of the well), or other types of regions or areas (such as defined flat surfaces or locations on a substrate) that can otherwise confine templates (such as by direct or indirect binding to the flat surface or location).

Although the exemplary embodiments of background models factoring neighbor effects are discussed in the context of "nearest" neighbors, the models could also be extended to factor in effects from other subsets of more distant neighbors in addition to or instead of effects from more immediate neighbors. For example, the neighbors could be grouped according to distance from the central well, with a first group of neighbors representing immediate or closest neighbors and one or more other groups representing neighbors that are more distant, which groups could be arranged concentrically. In some embodiments, the effects of different groups of neighbors could be weighed differently according to their distance relative to the central well.

Although the exemplary embodiments of background models generally treat the neighbors equally, the models could also be treated different based on an empirical observation that in some cases the local neighbors might not all contribute equally to the local headspace above the wells. For example, the velocity of the fluid above the wells might cause 'upstream' wells to contribute slightly more than 'downstream' wells. To reflect this, Equation NN6 could be modified as follows:

Eqn. NN7

$$s_c = Rs_e + \frac{(\gamma-1)}{\gamma\tau_c}\int s_e - s_c + \frac{\int \sum_{nn=1}^{N_{nn}}a_{nn}(s_{nn-c} - s_{nn-e})}{\gamma\tau_c} + \frac{1}{\beta_c}\int \phi_i + \frac{\tau_T}{\gamma\beta_c}\phi_i$$

where the additional terms $a_{nn}$ are scaling factors that modify the effect of each neighbor independently in order to account for them not all equally contributing to the signal in the headspace above the central well.

According to an exemplary embodiment, there is provided a method of modeling a background signal when sequencing a polynucleotide strand using sequencing-by-synthesis, comprising: flowing a series of nucleotide flows onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; receiving output signals from the reactor array; and modeling a background signal for the loaded reaction confinement region using the received output signals and a model adapted to account at least for an exchange of ions between the one or more neighboring reaction confinement regions and a headspace adjacent the loaded reaction confinement region and the one or more neighboring reaction confinement regions.

In various embodiments, the model may be adapted to account at least for an exchange of ions between at least two neighboring reaction confinement regions and the headspace, between at least three neighboring reaction confinement regions and the headspace, between at least four neighboring reaction confinement regions and the headspace, or more. The model may be adapted to account at least for an exchange of ions between six neighboring reaction confinement regions and the headspace, the six neighboring reaction confinement regions being arranged hexagonally around the loaded reaction confinement region.

The model may reflect a relationship between the loaded reaction confinement region, the neighboring reaction confinement regions, and a bulk fluid, all interacting with each other through the headspace. The model may be further adapted to account at least for an exchange of ions between the headspace and a bulk fluid.

In various embodiments, the model may be derived using a first characteristic equation representing conservation of protons in the headspace. The first characteristic equation may be Eqn. NN1, where $S_{nn}$ represents a proton concentration in each of the neighboring reaction confinement regions; $S_c$ represents a proton concentration in the loaded reaction confinement region; $S_T$ represents a proton concentration in the headspace; Shulk represents a proton concentration in a bulk fluid; $\alpha_w$ represents a resistance to proton movement between individual reaction confinement regions and the headspace; $\alpha_{bulk}$ represents a resistance to proton movement between the headspace and the bulk fluid; $\beta_T$ represents a buffer capacity of the headspace; and $N_{nn}$ represents a number of the neighboring reaction confinement regions. The first characteristic equation may comprise a term related to a difference between a proton concentration in each of the neighboring reaction confinement regions and a proton concentration in the headspace, a term related to a difference between a proton concentration in a bulk fluid and a proton concentration in the headspace, and/or a term related to a difference between a proton concentration in the loaded reaction confinement region and a proton concentration in the headspace.

In various embodiments, the model may be further derived using a second characteristic equation representing conservation of protons in the loaded reaction confinement region. The second characteristic equation may be Eqn. NN3a, where $S_c$ represents a proton concentration in the loaded reaction confinement region; $S_T$ represents a proton concentration in the headspace; $\alpha_w$ represents a resistance to proton movement between individual reaction confinement regions and the headspace; $\varphi_i$ represents a flux of protons generated by a nucleotide incorporation reaction; and $\beta_c$ represents a buffer capacity of the loaded reaction confinement region.

In various embodiments, the model may comprise an equation describing a relationship between the loaded reaction confinement region, the neighboring reaction confinement regions, and a bulk fluid, all interacting with each other through the headspace. The equation may be Eqn. NN5, where $\gamma=(N_{nn}+1+\alpha_w/\alpha_{bulk})$, $\tau_c=\alpha_w\beta_c$, and $\tau_T=\alpha_w\beta_T$; $S_{nn}$ represents a proton concentration in each of the neighboring reaction confinement regions; $S_c$ represents a proton concentration in the loaded reaction confinement region; $S_{bulk}$ represents a proton concentration in a bulk fluid; $\alpha_w$ represents a resistance to proton movement between individual reaction confinement regions and the headspace; $\alpha_{bulk}$ represents a resistance to proton movement between the headspace and the bulk fluid; $\beta_T$ represents a buffer capacity of the headspace; $\beta_c$ represents a buffer capacity of the loaded reaction confinement region; $N_{nn}$ represents a number of the neighboring reaction confinement regions; and $\varphi_i$ represents a flux of protons generated by a nucleotide incorporation reaction.

In various embodiments, the model may comprise a simplified equation describing a relationship between the loaded reaction confinement region, the neighboring reaction confinement regions, and a bulk fluid, all interacting with each other through the headspace, and the simplified equation may be Eqn. NN6, where $R=\tau_e/\tau_c$, $\tau_e=\alpha_e\beta_e$, $\tau_c=\alpha_c\beta_c$; $\tau_T=\alpha_w\beta_T$; $S_{nn-c}$ represents a proton concentration in each of the neighboring reaction confinement regions that is loaded; $S_{nn-e}$ represents a proton concentration in each of the neighboring reaction confinement regions that is not loaded; $S_c$ represents a proton concentration in the loaded reaction confinement region; $S_e$ represents a proton concentration in an empty reaction confinement region; $\beta_c$ represents a buffer capacity of the loaded reaction confinement region; $N_{nn}$ represents a number of the neighboring reaction confinement regions; $\varphi_i$ represents a flux of protons generated by a nucleotide incorporation reaction, and gamma is a unitless constant that indicates the sensitivity of the headspace to the effects of neighboring reaction confinement regions.

According to an exemplary embodiment, there is provided a non-transitory machine-readable storage medium comprising instructions which, when executed by a processor, cause the processor to: receive output signals relating to chemical reactions resulting from the flow of a series of nucleotides onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; and determine a background signal for the loaded reaction confinement region using the received output signals and a model adapted to account at least for an exchange of ions between the one or more neighboring reaction confinement regions and a headspace adjacent the loaded reaction confinement region and the one or more neighboring reaction confinement regions. In an embodiment, the model may be adapted to account at least for an exchange of ions between six neighboring reaction confinement regions and the headspace, the six neighboring reaction confinement regions being arranged hexagonally around the loaded reaction confinement region.

According to an exemplary embodiment, there is provided a method of sequencing a polynucleotide strand, comprising: flowing a series of nucleotide flows onto a reactor array having multiple reaction confinement regions, one or more copies of the polynucleotide strand being located in a loaded reaction confinement region of the reactor array, the loaded reaction confinement region being located in a vicinity of one or more neighboring reaction confinement regions that may or may not be loaded; receiving output signals from the reactor array; and determining a background signal for the loaded reaction confinement region using the received output signals and a model of an output signal from the loaded reaction confinement region, the model adapted to account at least for a direct or indirect exchange of ions between the loaded reaction confinement region and the one or more neighboring reaction confinement regions.

Figure 7A:
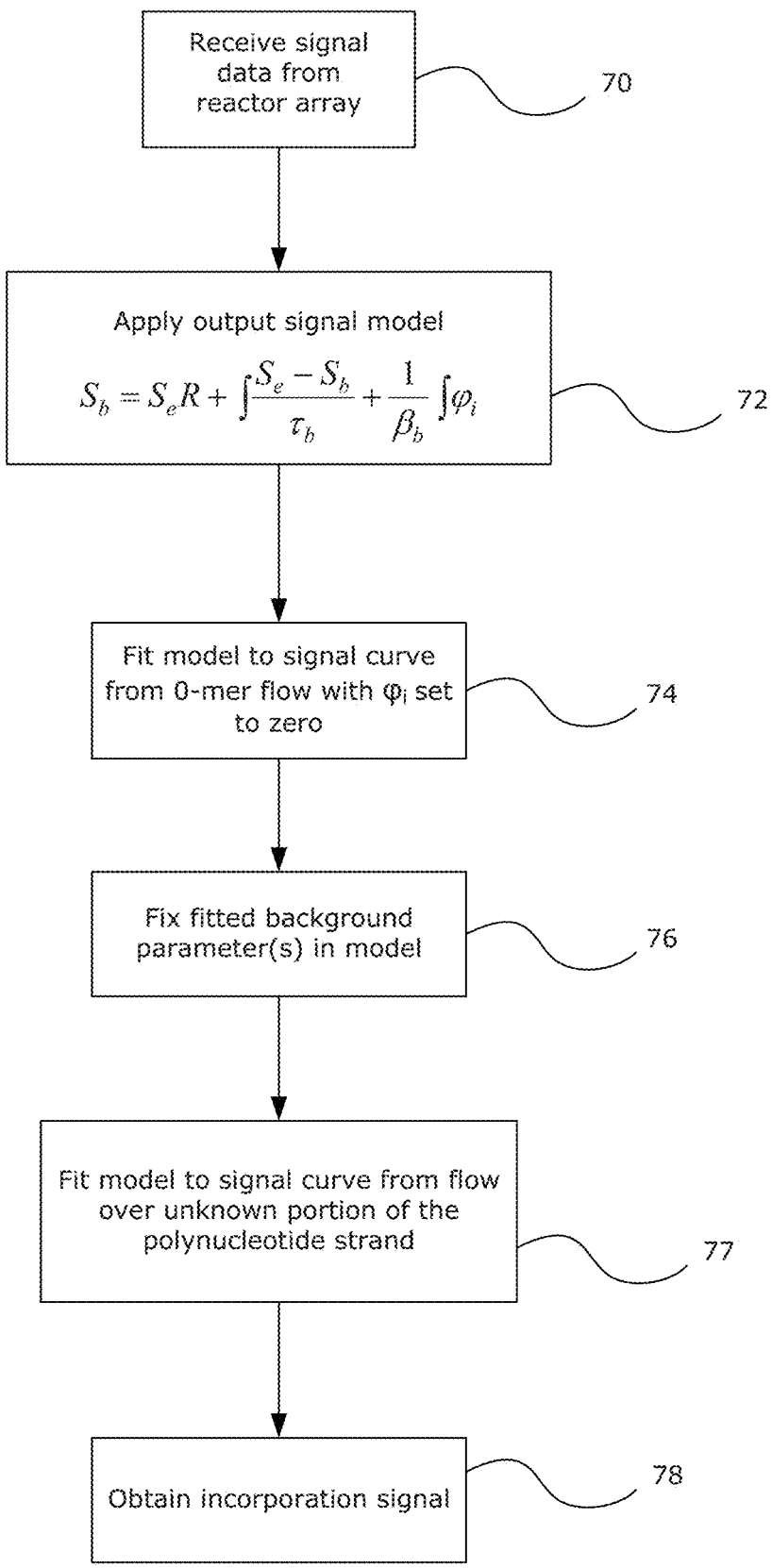
FIG. 7A shows a flowchart illustrating a method according to an exemplary embodiment.

FIG. 7A shows a flow chart illustration of an exemplary embodiment. As shown in step 70, signal data is received from a reactor array. As shown in step 72, the output signal model is applied to the signal data. As shown in step 74, the model is fit to the signal curve from a 0-mer flow with (pi set to zero. As shown in steps 76 and 77, the fitted parameters of the background component of the model are fixed and the model is then fitted to the signal curve from a nucleotide flow over an unknown portion of the sequence of the polynucleotide strand. As shown in step 78, by this fitting, the incorporation signal is obtained.

Figure 7B:
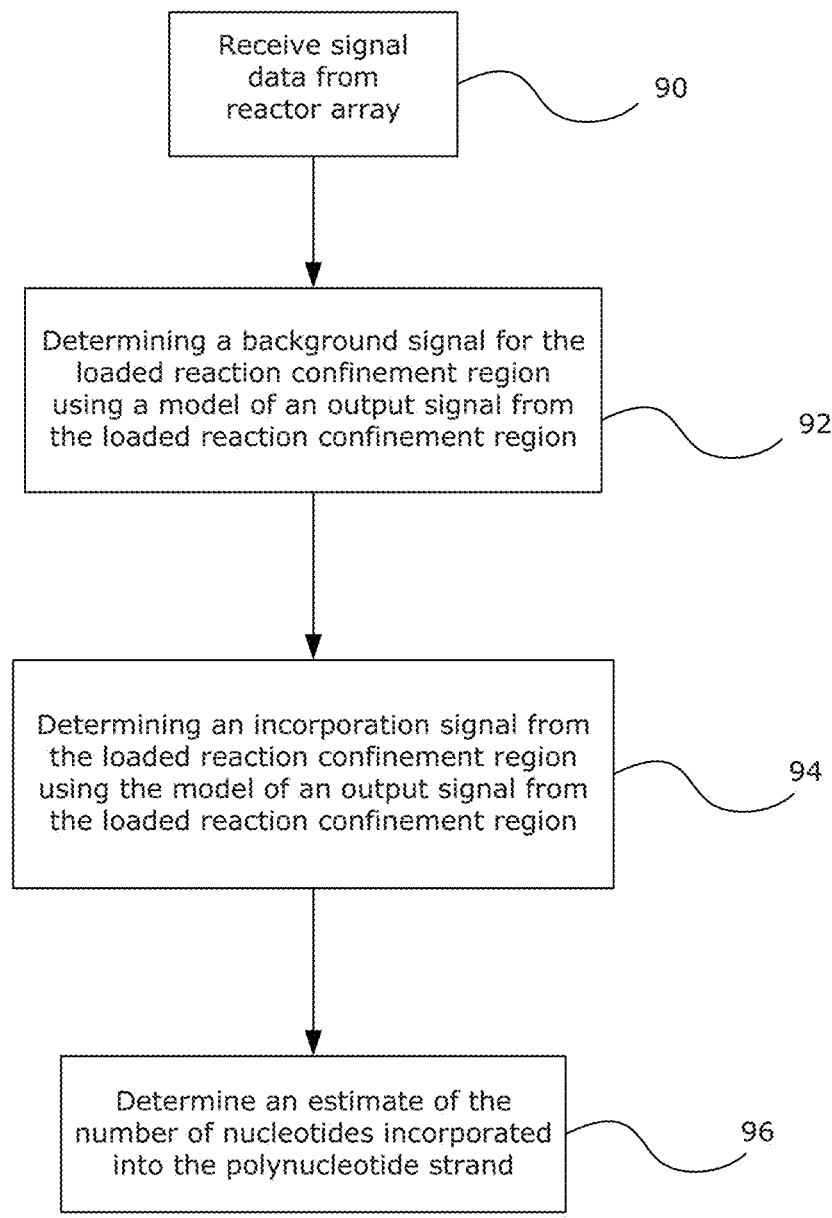
FIG. 7B shows a flowchart illustrating a method according to another exemplary embodiment.

FIG. 7B shows a flow chart illustration of another exemplary embodiment. As shown in step 90, signal data is received from a reactor array. As shown in step 92, a background signal for the loaded reaction confinement region is determined using a model of an output signal from the loaded reaction confinement region. As shown in step 94, an incorporation signal from the loaded reaction confinement region is determined using the model of an output signal from the loaded reaction confinement region. As shown in step 96, an estimate of the number of nucleotides incorporated into the polynucleotide strand is determined.

The incorporation signal obtained from the above-described process can be analyzed in any suitable manner to estimate the number of nucleotides incorporated into the polynucleotide strand. In some cases, the peak of the incorporation signal curve may be used to estimate the number of nucleotides incorporated into the polynucleotide strand. In some cases, the incorporation signal may be analyzed empirically by comparing to a set of reference signal curves. For example, the incorporation signal may be read by a "shape dictionary" with each signal shape being assigned to an estimated number of nucleotides incorporated into the polynucleotide strand. In some cases, the incorporation signals may be analyzed using a mathematical model of the incorporation signal.

In an exemplary embodiment, there is provided a mathematical model for the incorporation signal from the well of a reactor array. The incorporation signal may be obtained in any suitable way, including the techniques described above, or any other suitable technique, such as subtracting the 0-mer signal (as the background) from a different non-incorporating flow of the same well, or subtracting the 0-mer signal (as background) obtained from neighboring wells, or subtracting the signal from neighboring empty wells from the output signals.

The incorporation signal may depend on various conditions, such as the amount of nucleotide in the bulk nucleotide reagent solution and/or in the well, the amount of polymerase (e.g. number of polymerases, concentration of polymerases, or polymerase activity), the homopolymer n-mer length, and/or the rate of nucleotide diffusion. The incorporation signal model may include one or more equations that describe one or more of these parameters as well as relationships therebetween. The model may be a non-linear model in which one or more of the equations are non-linear. For example, the model may comprise a non-linear system of differential equations. The model may include equations for one or more of the following: the rate of change in the nucleotide amount in the loaded well, the amount of active polymerase in the well, the rate of change in the amount of active polymerase in the loaded well, or the flux of hydrogen ions generated by a nucleotide incorporation reaction.

The rate of change in the nucleotide amount in a loaded well may be expressed as being related to the rate of nucleotide diffusion into the well and the rate of nucleotide consumption by polymerase-catalyzed incorporation reactions. For example, the rate of change may be expressed as being proportional to the difference in the amount of nucleotide in the nucleotide reagent and the amount of nucleotide in the loaded well. The rate of nucleotide consumption may be expressed as being proportional to the amount of nucleotide in the loaded well multiplied by the amount of polymerase in the loaded well.

An equation for the amount of active polymerase in the well may include a parameter for the homopolymer n-mer length. The rate of change in the amount of active polymerase in the loaded well may be expressed as being related to the amount of nucleotide in the loaded well. The flux of hydrogen ions generated by a nucleotide incorporation reaction may be expressed as being related to the number of active polymerases, as limited by the amount of nucleotide in the loaded well. For example, the flux may be expressed as being proportional to the number of active polymerases multiplied by the amount of nucleotide in the loaded well. An equation for the flux of hydrogen ions may include a parameter relating to the rate of polymerase activity (e.g. a reaction rate coefficient).

An example of a system of non-linear differential equations according to an exemplary embodiment is shown in Equations 15-19 as follows. Equation 15 below expresses the rate of change of the nucleotide concentration in the well as being proportional to the concentration gradient, minus the rate at which the nucleotides are consumed by the polymerase-catalyzed reactions. In Equation 15, [dNTP] is the concentration of the nucleotide in the well; $[dNTP]_{top}$ is the concentration of the nucleotide in the bulk nucleotide reagent solution; "D" is the diffusion coefficient of the nucleotide; "k" is the reaction rate coefficient for polymerase activity; [A] is the number of polymerases in the well.

$$\frac{d[dNTP]}{dt} = D\{[dNTP]_{top} - [dNTP]\} - k[dNTP][A] \qquad \text{Eqn. 15}$$

Equation 16 below expresses the number of polymerases as being the sum of the numbers at each position along the homopolymer length M, where $[a_n]$ is the number of polymerases having "n" bases remaining along the homopolymer length. For example, $a_3$ is the number of polymerases that are located at a position on the polynucleotide strand where 3 additional base incorporations are needed to complete the homopolymer length.

$$[A] = \Sigma_{n=1}^{M}[a_n] \qquad \text{Eqn. 16:}$$

At the beginning of the reaction, all polymerases have M bases remaining and $[A]=[a_M]$. As the reaction progresses and nucleotide bases are incorporated into each polynucleotide strand, the number of polymerases at base position M decreases at a rate described by Equation 17 below. The rate of change of the number of polymerases at base position M is proportional to the nucleotide concentration and the number of polymerases with M additional base incorporations needed to complete the homopolymer length.

$$\frac{d[a_n]}{dt} = -k[dNTP][a_n], n = M \qquad \text{Eqn. 17}$$

At the beginning of the reaction, no nucleotide bases have yet been incorporated and all $[a_n]$ where n<M are zero. The population of polymerase at each of these positions $[a_n]$, where n<M, increases as polymerase from position $[a_{n+1}]$ incorporates a nucleotide base. The population of polymerase at each of these positions $[a_n]$ simultaneously decreases as these polymerase incorporate nucleotides. Equation 18 below expresses the rate of change of [an], where n<M, as being the difference between these two rates. [an] increases according to the rate of incorporation of base position $[a_{n+1}]$, which is proportional to [dNTP] and the number of polymerases at base position $[a_{n+1}]$. $[a_n]$ decreases according to the rate of incorporation of base position $[a_n]$, which is proportional to [dNTP] and the number of polymerase at base position $[a_n]$.

$$\frac{d[a_n]}{dt} = -k[dNTP]\{[a_{n+1}] - [a_n]\}, n < M \qquad \text{Eqn. 18}$$

Equation 19 below expresses the flux of hydrogen ions generated by the polymerase-catalyzed incorporation reaction as being related to the rate of polymerase activity, the concentration of nucleotide in the well, and the number of active polymerases.

$$\varphi_I = k[dNTP][A] \quad \text{Eqn. 19:}$$

Figure 8A:
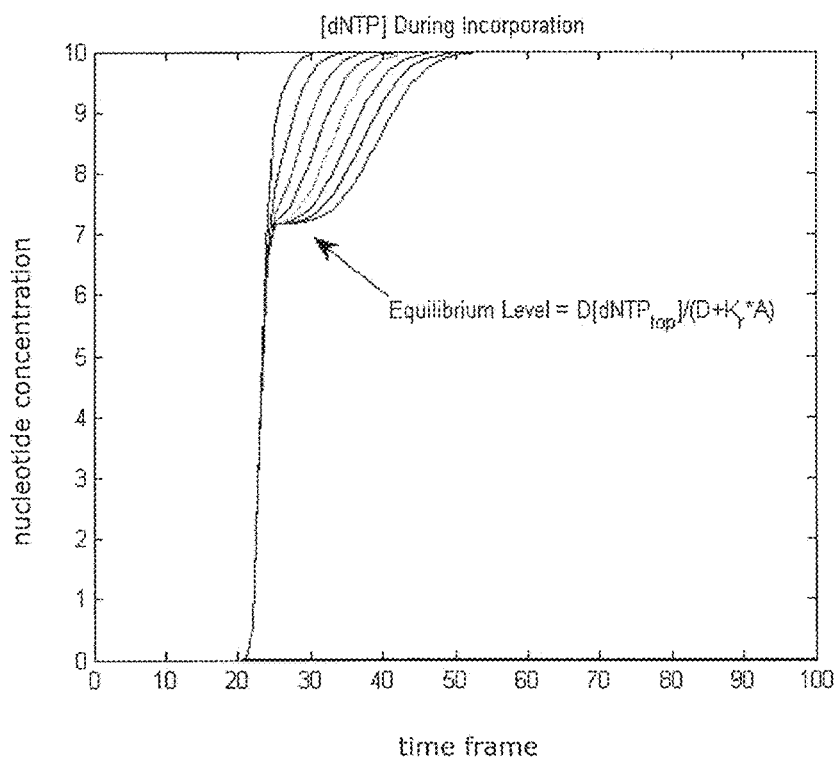

FIGS. 8A-8D show some of the behavioral characteristics of this particular model. FIG. 8A shows an example of how the nucleotide concentration in the well increases with the flow of the nucleotide reagent onto the reactor array, as affected by the consumption of the nucleotides by the polymerase-catalyzed incorporation reactions. In this example, the arrow shows a temporary equilibrium point where the rate of nucleotide diffusion into the well equals the rate at which the nucleotides are consumed. The leftmost curve represents a non-incorporation event (0-mer), whereas the rightmost curve represents the incorporation of 7 nucleotide bases (7-mer) into the template. The curves in between, from left to right, represent incorporation reactions for n-mer lengths of 1-mer, 2-mer, and so on. As seen here, the nucleotide concentration increases at a slower rate for incorporation reactions for longer n-mer lengths due to the higher rate and/or sustained duration of nucleotide consumption.

Figure 8B:
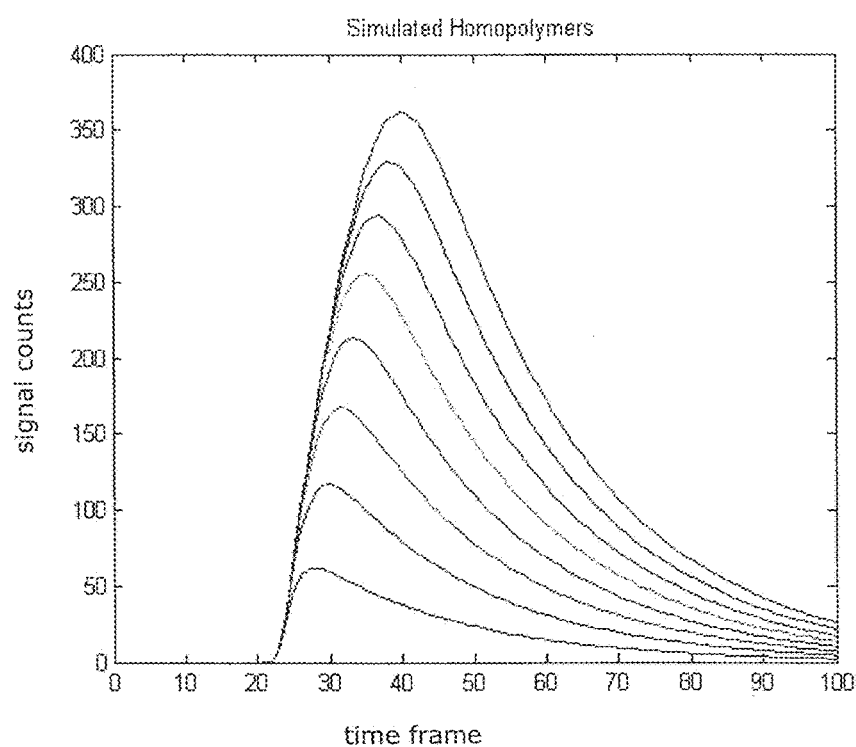

FIG. 8B shows an example of how the signal curves vary for incorporation reactions on different n-mer lengths. The bottommost curve represents a non-incorporation event (0-mer), whereas the topmost curve represents the incorporation of 7 nucleotide bases (7-mer) into the template. The curves in between, from bottom to top, represent incorporation reactions for n-mer lengths of 1-mer, 2-mer, and so on. As seen here, the signal curve is higher for incorporation reactions for longer n-mer lengths.

FIG. 8C shows an example of how the number of active polymerases decreases as the reaction progresses. The leftmost curve represents a non-incorporation event (0-mer), whereas the rightmost curve represents the incorporation of 7 nucleotide bases (7-mer) into the template. The curves in between, from left to right, represent incorporation reactions for n-mer lengths of 1-mer, 2-mer, and so on. As seen here, the number of active polymerases declines at a slower rate for incorporation reactions of longer n-mer lengths due to the longer duration needed to complete the multiple nucleotide incorporations.

FIG. 8D shows an example of how incorporation reactions can be limited by the amount of polymerase or the amount of nucleotide. In this example, the ratio of nucleotide diffusion rate versus polymerase activity ($D/K_r$) is varied. The leftmost curve represents a relatively higher nucleotide diffusion rate, but a relatively lower polymerase activity. The rightmost curve represents a relatively lower nucleotide diffusion rate, but a relatively higher polymerase activity. The curves in between represent intermediate conditions. As seen here, the incorporation reaction rate (as measured by the nucleotide concentration in the well) becomes limited by polymerase activity when the nucleotide/polymerase ratio is high, and becomes limited by nucleotide diffusion when the nucleotide/polymerase ratio is low.

The above-described incorporation signal model can be refined in various ways for improved computational efficiency. In particular, calculating the population of polymerase in each base position can be computationally inefficient. In one approach to simplifying this problem, the desired output of the incorporation model can be seen as the total number of hydrogen ions generated as a function of time. In this approach, the total number of active polymerase [A] and the nucleotide concentration [dNTP] are modeled, but the populations of the intermediate states [$a_n$] are only necessary in order to obtain [A]. Thus, instead of modeling the intermediate states [$a_n$], [A] can be directly computed by modeling each template strand as a non-homogeneous Poisson process. If the incorporation of each base is treated as a Poisson process with a non-homogenous rate of k[dNTP], then the expression for [A] can be given by Equation 20:

$$[A] = [A]_{t=0} \left\{ e^{-\int_0^t k[dNTP]} \sum_{i=0}^{M-1} \frac{\left(\int_0^t k[dNTP]\right)^i}{i!} \right\} \quad \text{Eqn. 20}$$

where $[A]_{t=0}$ is the starting number of active polymerase in the well before any nucleotides have been incorporated, and the expression in brackets is a cumulative Poisson equation that calculates the probability that any given polynucleotide strand has not yet completed all M bases of the homopolymer incorporation. This simplification may eliminate the need to use Equations 16, 17, and 18 because they are implicitly captured as part of the Poisson process. Equations 15 and 19 are still used to model the diffusion of [dNTP] and the generation of hydrogen ions. This simplified version of the incorporation model may produce the same results as the more complex form (i.e., they can be equivalent models).

In another approach to refining the incorporation signal model, the rate of incorporation can be modified to behave according to a Michaelis-Menten kinetic model of the polymerization reaction. In order to adapt the model with Michaelis-Menten kinetics, the k[dNTP] terms in Equations 15 and 17-20 can be replaced by $k[dNTP]/(k_m+[dNTP])$, where $k_m$ is the [dNTP] at which the reaction rate is at half of its maximum value.

The incorporation signal model can then be fitted to the incorporation signal data. The fitting may involve solving the equation(s) in the model to fit the incorporation signal data. This fitting of the incorporation signal model may establish one or more parameters of the model. For example, the fitting may involve varying the parameter for the homopolymer n-mer length to find a value that improves (e.g. optimizes) the model fit to the incorporation signal data. For example, the above set of equations can be solved for [A] and/or M (i.e. the estimated homopolymer length).

As explained above, any suitable fitting technique can be used. Also as explained above, this fitting of the incorporation signal model can encompass any suitable portion of the incorporation signal data. For example, one or more data points at an earlier time frame may be given a greater weight than one or more data points at a later time frame in the fitting process.

Figure 9:
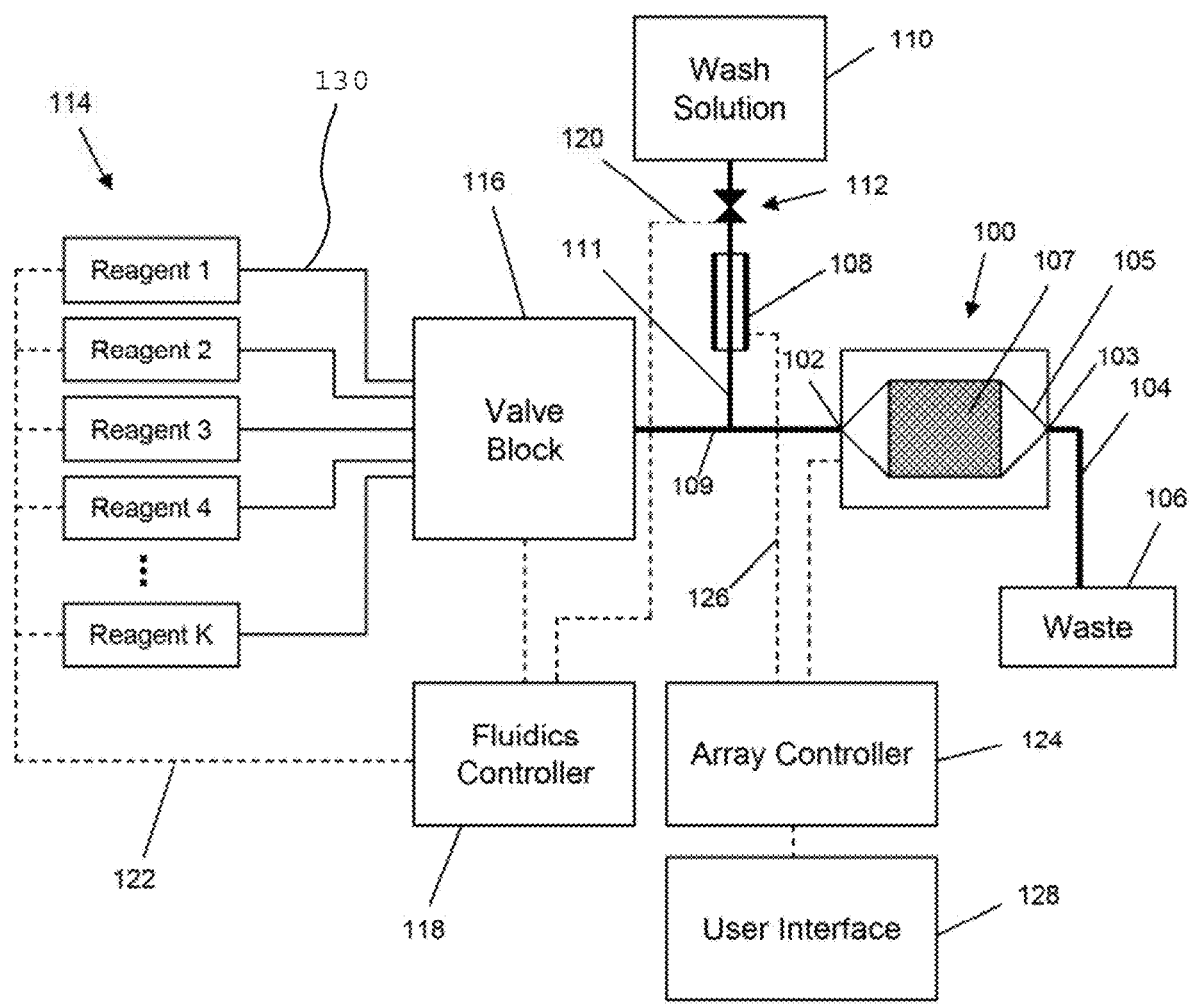
FIG. 9 is a diagram showing a sequencing apparatus according to an exemplary embodiment.

According to an exemplary embodiment, there is provided an apparatus for sequencing polynucleotide strands according to the above-discussed exemplary methods. A particular example of an apparatus is shown in FIG. 9. The apparatus of FIG. 9 is configured for pH-based sequencing and includes multiple reservoirs for containing nucleotide reagents 1 through K (114). These reagents contain the nucleotides to be flowed for the sequencing process. The reagents 114 are flowed through fluid passages 130 and through a valve block 116 that controls the flow of the reagents to flow chamber 105 (also referred to herein as a reaction chamber) via fluid passage 109. The apparatus includes a reservoir 110 for containing a wash solution that is used to wash away the nucleotide reagent of the previous step. Reagents are discarded through waste passage 104 into a waste container 106 after exiting the flow chamber 105.

The apparatus also includes a fluidics controller 118, which may programmed to control the flow from the multiple reagent reservoirs to the flow chamber according to a predetermined ordering that comprises an alternate flow ordering, as described above. For this purpose, fluidics controller 118 may be programmed to cause the flow of reagents 114 from the reagents reservoir and operate the valves 112 and 116. The fluidics controller may use any conventional instrument control software, such as LabView (National Instruments, Austin, Tex.). The reagents may be driven through the fluid pathways 130, valves, and flow cell by any conventional mechanism such as pumps or gas pressure.

The apparatus also has a valve 112 for controlling the flow of wash solution into passage 109. When valve 112 is closed, the flow of wash solution is stopped, but there is still uninterrupted fluid and electrical communication between reference electrode 108, passage 109, and sensor array 100. Some of the reagent flowing through passage 109 may diffuse into passage 111, but the distance between reference electrode 108 and the junction between passages 109 and 111 is selected so that little or no amount of the reagents flowing in common passage 109 reach reference electrode 108. This configuration has the advantage of ensuring that reference electrode 108 is in contact with only a single fluid or reagent throughout an entire multi-step reaction process.

As shown in FIG. 9, flow chamber 105 is loaded with a flow cell that includes an inlet 102, an outlet 103, and a microwell array 107 which is operationally associated with a sensor array 100 that measures physical and/or chemical parameters in the microwells that provide information about the status of a reaction taking place therein; or in the case of empty wells, information about the physical and/or chemical environment in the flow cell. Each microwell may have a sensor for detecting an analyte or reaction property of interest. In this particular embodiment, the microwell array is integrated with the sensor array as a single chip. A flow cell can have a variety of designs for controlling the path and flow rate of reagents over the microwell array. This particular apparatus has an array controller 124 which receives information from sensor array 100 and reference electrode 108 via communication line 126. A user interface 128 provides an interface through which a user may interact with the apparatus.

Figure 10:
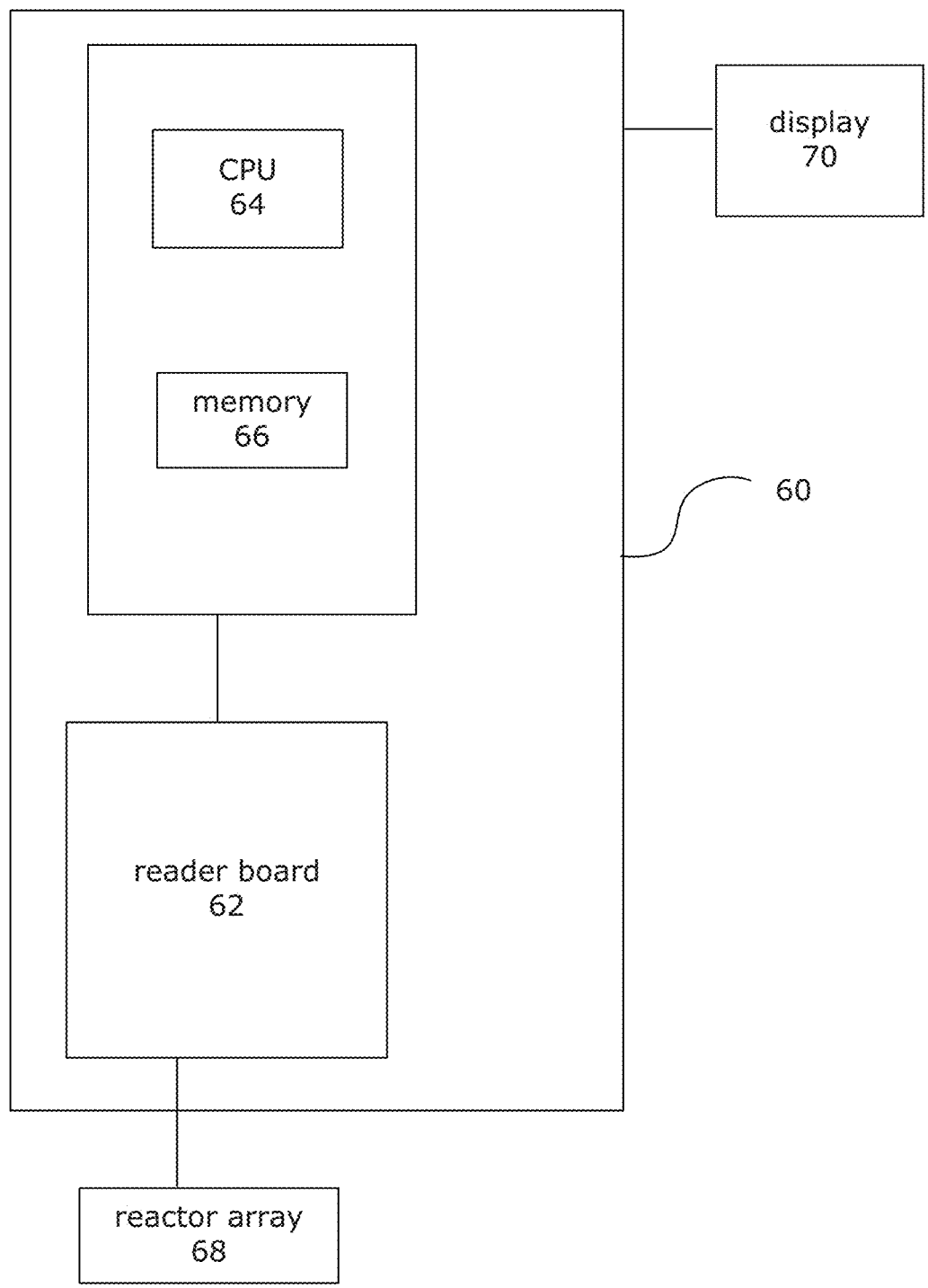
FIG. 10 shows an apparatus according to an exemplary embodiment.

An apparatus may be used to perform the above-described exemplary methods. The apparatus may be a computer that includes various components such as processor(s) and memory. An example of an apparatus of the present teachings is shown in FIG. 10. In some embodiments, the apparatus 60 may include one or more processors 64 and machine-readable memory 66. In some embodiments, the apparatus may include a display 70. In some embodiments, the apparatus may include a reader board 62 which is coupled to a reactor array 68. The reader board 62 may include various components used in signal processing, including analog-to-digital converters. In some embodiments the apparatus may be part of the sequencing apparatus. In other embodiments, the apparatus may be separate from the sequencing apparatus; in some embodiments the apparatus may be coupled to the sequencing apparatus.

In pH-based detection methods, the production of hydrogen ions may be monotonically related to the number of contiguous complementary bases in the template strands (as well as the total number of template strands with primer and polymerase that participate in an extension reaction). Thus, when there is a number of contiguous identical complementary bases in the template (i.e. a homopolymer region), the number of hydrogen ions generated is generally proportional to the number of contiguous identical complementary bases. The corresponding output signals may sometimes be referred to as "1-mer", "2-mer", "3-mer" output signals, and so on, based on the expected number of repeating bases. The term "n-mer" refers to the number of contiguous identical complementary bases that are incorporated into the complementary strand on the template strand. Where the next base in the template is not complementary to the flowed nucleotide, generally no incorporation occurs and there is no substantial release of hydrogen ions (in which case, the output signal is sometimes referred to as a "0-mer" output signal).

Figure 11:
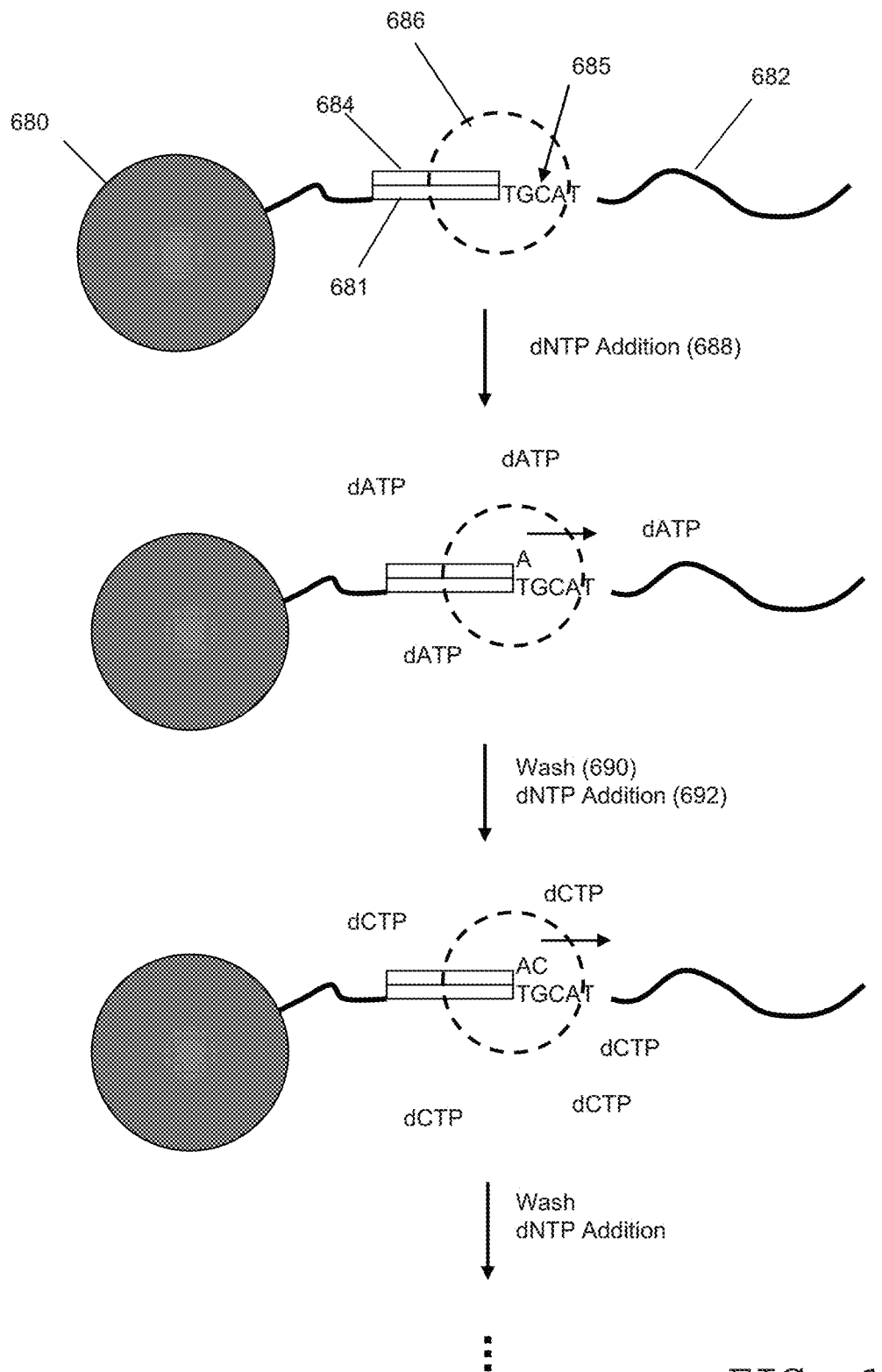
FIG. 11 shows an example of a sequencing-by-synthesis operation.

In each wash step of the cycle, a wash solution (typically having a predetermined pH) is used to remove residual nucleotide of the previous step in order to prevent miscorporations in later cycles. Usually, the four different kinds of nucleotides (e.g. dATP, dCTP, dGTP, and dTTP) are flowed sequentially to the reaction chambers, so that each reaction is exposed to one of the four different nucleotides for a given flow, with the exposure, incorporation, and detection steps being followed by a wash step. An example of this process is illustrated in FIG. 11, which shows a template polynucleotide strand 682 attached to a particle 680. Primer 684 is annealed to template strand 682 at its primer binding site 681. A DNA polymerase 686 is operably bound to the template-primer duplex. Template strand 682 has the sequence 685, which is awaiting complementary base incorporation. Upon the flow of the nucleotide (shown as dATP), polymerase 686 incorporates a nucleotide since "T" is the next nucleotide in template strand 682 (because the "T" base is complementary to the flowed dATP nucleotide). Wash step 690 follows, after which the next nucleotide (dCTP) is flowed 692. Optionally, after each step of flowing a nucleotide, the reaction chambers may be treated with a nucleotide-destroying agent (such as apyrase) to eliminate any residual nucleotides remaining in the chamber, which can cause spurious extensions in subsequent cycles. This process may be repeatedly continued with additional flows of nucleotide reagents.

In various embodiments, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

Polynucleotides may comprise the four natural nucleosides (e.g. deoxyadenosine, deoxycytidine, deoxyguanosine, deoxythymidine for DNA or their ribose counterparts for RNA) linked by phosphodiester linkages. However, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity (e.g. single stranded DNA, RNA/DNA duplex, or the like), then selection of an appropriate composition for the oligonucleotide or polynucleotide substrates is well within the knowledge of one of ordinary skill, especially with guidance from treatises such as Sambrook et al, MOLECULAR CLONING, 2nd ed. (Cold Spring Harbor Laboratory, New York, 1989), and like references.

"Polynucleotide" refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. As used herein, the term "oligonucleotide" refers to smaller polynucleotides, for example, having 5-40 monomeric units.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like, including any medium suitable for use in a computer. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

According to other embodiments of the present teachings, any one or more features of any one or more of the above-discussed teachings and/or exemplary embodiments may be performed or implemented at least partly using a cloud computing resource.

Those skilled in the art may appreciate from the foregoing description that the present teachings may be implemented in a variety of forms, and that the various embodiments may be implemented alone or in combination. Therefore, while the embodiments of the present teachings have been described in connection with particular examples thereof, the true scope of the embodiments and/or methods of the present teachings should not be so limited since other modifications will become apparent to the skilled practitioner upon a study of the drawings, specification, and following claims.

What is claimed is:

1. A system for sequencing-by-synthesis, comprising:
a reactor array having multiple reaction confinement regions, one or more copies of a polynucleotide strand being located in a loaded reaction confinement region of the reactor array, the loaded reaction confinement region being located in a vicinity of one or more neighboring reaction confinement regions;
a machine-readable memory; and
a processor communicatively coupled to the reactor array and the memory, the processor configured to execute machine-readable instructions, which, when executed by the processor, cause the system to perform a method, comprising:
receiving output signals at the processor from the reactor array in response to flowing a series of nucleotide flows onto the reactor array, and
estimating a background signal for the loaded reaction confinement region using the received output signals and a background model representing at least an exchange of ions between the one or more neighboring reaction confinement regions and a headspace adjacent to the loaded reaction confinement region and the one or more neighboring reaction confinement regions, wherein the background model is derived using a first characteristic equation, wherein the first characteristic equation comprises a term related to a difference between a proton concentration in each of the neighboring reaction confinement regions and a proton concentration in the headspace.

2. The system of claim 1, wherein the background model represents at least an exchange of ions between at least two neighboring reaction confinement regions and the headspace.

3. The system of claim 1, wherein the background model represents at least an exchange of ions between at least three neighboring reaction confinement regions and the headspace.

4. The system of claim 1, wherein the background model represents at least an exchange of ions between at least four neighboring reaction confinement regions and the headspace.

5. The system of claim 1, wherein the background model represents at least an exchange of ions between six neighboring reaction confinement regions and the headspace, the six neighboring reaction confinement regions being arranged hexagonally around the loaded reaction confinement region.

6. The system of claim 1, wherein the background model simulates a relationship between the loaded reaction confinement region, the neighboring reaction confinement regions, and a bulk fluid, all interacting with each other through the headspace.

7. The system of claim 1, wherein the background model represents at least an exchange of ions between the headspace and a bulk fluid.

8. The system of claim 1, wherein the first characteristic equation represents a conservation of protons in the headspace.

9. The system of claim 8, wherein the first characteristic equation is:

where $S_{nn}$ represents the proton concentration in each of the neighboring reaction confinement regions; $S_c$ represents a proton concentration in the loaded reaction confinement region; $S_T$ represents the proton concentration in the headspace; $S_{bulk}$ represents a proton concentration in a bulk fluid; $\alpha_w$ represents a resistance to proton movement between individual reaction confinement regions and the headspace; $\alpha_{bulk}$ represents a resistance to proton movement between the headspace and the bulk fluid; $\beta_T$ represents a buffer capacity of the headspace; and $N_{nn}$ represents a number of the neighboring reaction confinement regions.

10. The system of claim 8, wherein the first characteristic equation comprises a term related to a difference between a proton concentration in a bulk fluid and the proton concentration in the headspace.

11. The system of claim 8, wherein the first characteristic equation comprises a term related to a difference between a proton concentration in the loaded reaction confinement region and the proton concentration in the headspace.

12. The system of claim 8, wherein the background model is further derived using a second characteristic equation representing a conservation of protons in the loaded reaction confinement region.

13. The system of claim 12, wherein the second characteristic equation is:

$$\frac{s_T - s_c}{\alpha_w} + \phi_i = \beta_c \frac{ds_c}{dt}$$

where $S_c$ represents a proton concentration in the loaded reaction confinement region; $S_T$ represents the proton concentration in the headspace; $\alpha_w$ represents a resistance to proton movement between individual reaction confinement regions and the headspace; $\varphi_i$ represents a flux of protons generated by a nucleotide incorporation reaction; and $\beta_c$ represents a buffer capacity of the loaded reaction confinement region.

14. The system of claim 1, wherein the background model comprises an interaction equation representing a relationship between the loaded reaction confinement region, the neighboring reaction confinement regions, and a bulk fluid, all interacting with each other through the headspace.

15. The system of claim 14, wherein the interaction equation is:

where $\gamma=(N_{nn}+1+\alpha_w/\alpha_{bulk})$, $\tau_c=\alpha_w\beta_c$, and $\tau_T=\alpha_w/\beta_T$, $S_{nn}$ represents the proton concentration in each of the neighboring reaction confinement regions; $S_c$ represents a proton concentration in the loaded reaction confinement region; $S_{bulk}$ represents a proton concentration in the bulk fluid; $\alpha_w$ represents a resistance to proton movement between individual reaction confinement regions and the headspace; $\alpha_{bulk}$ represents a resistance to proton movement between the headspace and the bulk fluid; $\beta_T$ represents a buffer capacity of the headspace; $\beta_c$ represents a buffer capacity of the loaded reaction confinement region; $N_{nn}$ represents a number of the neighboring reaction confinement regions; and $\varphi_i$ represents a flux of protons generated by a nucleotide incorporation reaction.

16. The system of claim 1, wherein the background model comprises a simplified equation representing a relationship between the loaded reaction confinement region, the neighboring reaction confinement regions, and a bulk fluid, all interacting with each other through the headspace, the simplified equation being:

$$s_c = Rs_e + \frac{(\gamma-1)}{\gamma\tau_c}\int s_e - s_c + \frac{\int\sum_{nn=1}^{N_{nn}}(s_{nn-c} - s_{nn-e})}{\gamma\tau_c} + \frac{1}{\beta_c}\int \phi_i + \frac{\tau_T}{\gamma\beta_c}\phi_i$$

where $R=\tau_e/\tau_c$, $\tau_e=\alpha_e\beta_e$, $\tau_c=\alpha_c\beta_c$; $\tau_T=\alpha_w\beta_T$, $S_{nn-c}$ represents a proton concentration in each of the neighboring reaction confinement regions that is loaded; $S_{nn-e}$ represents a proton concentration in each of the neighboring reaction confinement regions that is not loaded; $S_c$ represents a proton concentration in the loaded reaction confinement region; $S_e$ represents a proton concentration in an empty reaction confinement region; $\beta_c$ represents a buffer capacity of the loaded reaction confinement region; $N_{nn}$ represents a number of the neighboring reaction confinement regions; $\varphi_i$ represents a flux of protons generated by a nucleotide incorporation reaction, and gamma is a unitless constant that indicates a sensitivity of the headspace to effects of neighboring reaction confinement regions.

17. The system of claim 16, wherein the background model comprises scaling factors $a_{nn}$ multiplied with proton concentration terms $(S_{nn-c}-S_{nn-e})$ in the simplified equation corresponding to different neighboring reaction confinement regions, wherein the scaling factors represent unequal contributions of ions exchanged with the headspace by the one or more neighboring reaction confinement regions.

18. The system of claim 1, wherein the processor is further configured to fit the background model to output signals resulting from a non-incorporation event in response to a nucleotide flow in the series of nucleotide flows.

* * * * *